(12) United States Patent
Strohm et al.

(10) Patent No.: US 8,907,135 B2
(45) Date of Patent: *Dec. 9, 2014

(54) MULTIHYDRIC COMPOUND DEHYDRATION SYSTEMS, CATALYST COMPOSITIONS, AND METHODS

(71) Applicant: Battelle Memorial Institute, Richland, WA (US)

(72) Inventors: James J. Strohm, Richland, WA (US); Alan H. Zacher, Richland, WA (US); James F. White, Richland, WA (US); Michel J. Gray, Richland, WA (US); Vanessa Lebarbier, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/892,143

(22) Filed: May 10, 2013

(65) Prior Publication Data

US 2013/0253227 A1   Sep. 26, 2013

Related U.S. Application Data

(63) Continuation of application No. 12/973,518, filed on Dec. 20, 2010, now Pat. No. 8,530,703.

(60) Provisional application No. 61/288,158, filed on Dec. 18, 2009.

(51) Int. Cl.
| | |
|---|---|
| C07C 45/52 | (2006.01) |
| B01J 8/00 | (2006.01) |
| B01J 27/00 | (2006.01) |
| B01J 38/04 | (2006.01) |
| B01J 27/28 | (2006.01) |
| B01J 27/185 | (2006.01) |
| B01J 38/12 | (2006.01) |
| B01J 38/02 | (2006.01) |
| B01J 27/18 | (2006.01) |
| C07C 45/00 | (2006.01) |
| B01J 38/06 | (2006.01) |
| B01J 21/08 | (2006.01) |

(52) U.S. Cl.
CPC .............. C07C 45/00 (2013.01); B01J 38/04 (2013.01); C07C 45/52 (2013.01); B01J 27/285 (2013.01); B01J 27/1853 (2013.01); B01J 38/12 (2013.01); B01J 38/02 (2013.01); B01J 8/001 (2013.01); B01J 27/1806 (2013.01); B01J 21/08 (2013.01); B01J 27/18 (2013.01); B01J 38/06 (2013.01)
USPC .............. 568/486; 568/857; 502/34; 502/38; 502/213; 422/129

(58) Field of Classification Search
USPC ........ 568/486, 857; 502/34, 38, 213; 422/129
See application file for complete search history.

(56) References Cited

U.S. PATENT DOCUMENTS

| | | | |
|---|---|---|---|
| 2,516,627 | A | 7/1950 | Hearne et al. |
| 2,558,520 | A | 6/1951 | Hoyt et al. |
| 2,993,010 | A | 7/1961 | Guyer et al. |
| 3,197,483 | A | 7/1965 | Bernard Buchholz et al. |
| 3,893,946 | A | 7/1975 | Weisang et al. |
| 4,137,271 | A | 1/1979 | Stiles et al. |
| 4,234,752 | A | 11/1980 | Wu et al. |
| 4,632,916 | A | 12/1986 | Bither, Jr. |
| 4,642,394 | A | 2/1987 | Che |
| 4,649,205 | A | 3/1987 | Edwards et al. |
| 4,729,978 | A | 3/1988 | Sawicki |
| 5,387,720 | A | 2/1995 | Neher et al. |
| 5,426,249 | A | 6/1995 | Haas et al. |
| 5,753,716 | A | 5/1998 | Peng et al. |
| 7,396,962 | B1 | 7/2008 | Dubois et al. |
| 7,498,454 | B2 | 3/2009 | Redlingshoefer et al. |
| 7,683,220 | B2 | 3/2010 | Matsunami et al. |
| 7,846,861 | B2 | 12/2010 | Redlingshofer et al. |
| 2003/0149283 | A1 | 8/2003 | Manzer |
| 2007/0129570 | A1 | 6/2007 | Shima et al. |
| 2008/0146852 | A1 | 6/2008 | Dubois et al. |
| 2008/0183013 | A1 | 7/2008 | Dubois et al. |
| 2008/0183019 | A1 | 7/2008 | Redlingshofer et al. |
| 2008/0214384 | A1 | 9/2008 | Redlingshofer et al. |
| 2008/0214880 | A1 | 9/2008 | Dubois et al. |
| 2008/0319233 | A1 | 12/2008 | Dubois |
| 2009/0054538 | A1 | 2/2009 | Peterson et al. |
| 2009/0054693 | A1 | 2/2009 | Peterson et al. |
| 2009/0054694 | A1 | 2/2009 | Peterson et al. |
| 2009/0054695 | A1 | 2/2009 | Peterson et al. |
| 2009/0118549 | A1 | 5/2009 | Matsunami et al. |

FOREIGN PATENT DOCUMENTS

| | | |
|---|---|---|
| CN | 101119955 | 2/2008 |
| DE | 850 608 C | 8/1952 |
| DE | 23 25 051 A1 | 12/1974 |
| DE | 42 38 493 C1 | 4/1994 |

(Continued)

OTHER PUBLICATIONS

PCT/US2008/074079 IPRP, Feb. 24, 2010, Battelle Memorial Institute.
PCT/US2008/074079 Partial SR, Mar. 9, 2009, Battelle Memorial Institute.
PCT/US2008/074084 IPRP, Feb. 24, 2010, Battelle Memorial Institute.
PCT/US2008/074084 Partial S.R., May 20, 2009, Battelle Memorial Institute.
PCT/US2008/074084 S.R., Oct. 21, 2009, Battelle Memorial Institute.
PCT/US2008/074084 W.O., Oct. 21, 2009, Battelle Memorial Institute.

(Continued)

*Primary Examiner* — Sikarl Witherspoon
(74) *Attorney, Agent, or Firm* — Wells St. John P.S.

(57) ABSTRACT

The present disclosure relates to facilities, systems, methods and/or catalysts for use in chemical production. In particular, the disclosure provides innovations relating to dehydration of multihydric compounds such as glycerol to form acrolein. Some of these innovations include continuous reaction systems as well as system parameters that allow for long term production.

24 Claims, 28 Drawing Sheets

(56) References Cited

FOREIGN PATENT DOCUMENTS

| | | |
|---|---|---|
| EP | 0 447 033 | 9/1991 |
| EP | 0 509 927 | 10/1992 |
| EP | 0 598 228 | 10/1993 |
| EP | 0 598 229 | 10/1993 |
| EP | 1 044 949 | 10/2000 |
| EP | 2 157 074 | 2/2010 |
| FR | 695 931 A | 12/1930 |
| FR | 846063 | 9/1939 |
| FR | 2882053 | 1/2006 |
| FR | 2884818 | 10/2006 |
| GB | 2 093 060 A | 8/1982 |
| JP | 60 096513 | 5/1985 |
| JP | 2005213225 | 8/2005 |
| JP | 2008-530150 | 8/2008 |
| WO | WO 93/05006 | 3/1993 |
| WO | WO 99/05085 | 2/1999 |
| WO | WO 2006/087083 A2 | 8/2006 |
| WO | WO 2006/114506 A1 | 11/2006 |
| WO | WO 2007/058221 A1 | 5/2007 |
| WO | WO 2008/052993 | 5/2008 |
| WO | WO 2008/092534 | 8/2008 |
| WO | WO 2009/029535 | 3/2009 |
| WO | WO 2009/029541 A1 | 3/2009 |

OTHER PUBLICATIONS

PCT/US2008/074090 IPRP, Feb. 24, 2010, Battelle Memorial Institute.
PCT/US2008/074090 Partial SR, May 12, 2009, Battelle Memorial Institute.
PCT/US2008/074090 S.R., Jul. 28, 2009, Battelle Memorial Institute.
PCT/US2008/074090 W.O., Jul. 28, 2009, Battelle Memorial Institute.
PCT/US2008/074094 IPRP, Feb. 24, 2010, Battelle Memorial Institute.
PCT/US2008/074094 S.R., Feb. 5, 2009, Battelle Memorial Institute.
PCT/US2008/074094 W.O., Feb. 5, 2009, Battelle Memorial Institute.
PCT/US2010/061373 IPRP, Jun. 19, 2012, Battelle Memorial Institute.
PCT/US2010/061373 SearchReport, Oct. 7, 2011, Battelle Memorial Institute.
PCT/US2010/061373WrittenOpinio, Oct. 7, 2011, Battelle Memorial Institute.
Adkins et al., "Acrolein", Organic Syntheses, vol. 1 p. 6 1926, vol. 1 p. 15 1941, 4 pages.
Anon., "Modeling the reaction behavior of glycerol in sub- and supercritical water", Germany, 2000, 2 pgs.
Antal, Jr et al., "Heterolysis and Homolysis in Supercritical Water" American Chemical Society, 1985, pp. 78-87.
Barrault et al., "Selective Esterification . . . ", Chemical Industries, 1998, pp. 13-23.
Chai, Song-Hai et al., "Sustainable production of acrolein: Gas-phase dehydration of glycerol over Nb2O5 Catalyst", Journal of Catalysis 250 (2007) 342-349.
Clacens et al. "Selective etherification of glycerol to polyglycerols . . . ", Applied Catalysis, 2002, pp. 181-190.
Corma et al. Jour of Catalysis 247 (2007) 307-27.
Cottin et al. "Preparation de diglycerol et triglycerol . . . ", Fondmental, Oct. 1998, pp. 407-412.
Database CA, Xu, Bo-Qing et al: "Process for dehydration of polyhydric alcohols" (XP-002524780), Nippon Shokubai Co., Ltd., Japan (Chemical Abstracts Service, Columbus, OH), May 24, 2007.
Delaby, "Academie Des Sciences" Comptes Rendus, 1923, pp. 690-693.
Erlenmeyer et al., "Die Dissociation des Glycerins" Annalen Der Chemie, 1904, pp. 209-223.
Faro, Arnaldo C., et al, "Cumene hydrocracking and tiophene HDS on niobia-supported Ni, Mo and Ni—Mo catalaysts" Catalysis Today, vol. 118, 2006, pp. 402-409, XPOO2511927 Abstract.
Hanyu et al., "Manfacture of Acrolein", Journal of the Society of Chemical Industry, Japan, vol. 37 1934, p. 538.
Hauschild et al. "Contribution a l'etude de la deshydratation . . . ", Bulletin de la Societe Chimique de France, 1956, pp. 878-881.
Iditoiu C., et al.; "Non-isothermal Dehydration Kinetics of Some Cationites", Journal of Thermal Analysis and Calorimetry, Kluwer Academic Publishers, Dordrecht, NL, vol. 55, No. 3, Mar. 1, 1999, pp. 885-893.
Ishikawa et al., "Generation of Trace Amount of Acrolein Standard . . .", Bunseki Kagaku, The Japan Society for Analytical Chemistry, vol. 32 Oct. 1983, pp. E321-E325.
Katryniok, Benjamin, et al., "Towards the Sustainable Production of Acrolein by Glycerol Dehydration" ChemSusChem 2009, 2, 719-730.
Krammer et al., "Untersuchungen zum Synthese-potential . . . ", Chemie Ingenieur Technik, 1998, pp. 1559-1563.
Mishra, T, et al, "Transition metal promoted A1P04 catalyst 2. The catalytic activity of MO.05A10.95P04 for alcohol conversion and cumene cracking/dehydrogenation reactions," Applied Catalysis A: General, vol. 166, 1998, pp. 115-122, XP002511925 Abstract, Table 1.
Moureu et al., "Memoires et Communications", Comptes Rendus, 1919, pp. 885-889.
Nef, J.U., Annalen der Chemie 1904, 335, 209-223.
Ott et al., "Catalytic dehydration of glycerol . . . ", Green Chem., 2006, 8, 214-220 (NOTE: cited incorrectly on initial IDS as The Royal Society of Chemistry, 2006, pp. 214-220).
Ott et al., Chemie Ingenieur Technik, 2004, p. 1292.
Ramayya et al., "Acid-catalysed dehydration of alcohols in supercritical water", Fuel, Oct. 1987, vol. 66, pp. 1364-1371.
Rosenthaler, L., "Beitrage zum Nachnveis organischer Verbindungen", Pharmazeutische Zeitung-Nachrichten, 1954, pp. 464-466.
Sabatier et al., "Conformement A Une Decision De L'Accademie" Comptes Rendus, 1918, pp. 1003-1039.
Song, L et al, "A new route to prepare supported nickel phosphide/silica-alumina hydrotreating catalysts from amorphous alloys" Catalysis Today, vol. 125, Apr. 8, 2007, pp. 137-142, XPOO2511926 Abstract Table 1.
Song-Hai, C., et al., "Sustainable production of acrolein: investigation of solid acid-base catalysts for gas-phase dehydration of glycerol", Green Chemistry 2007, 9, 1130-1136.
Tsukuda et al.; "Production of Acrolein from Glycerol over Silica-supported Heteropoly Acids", Catalysis Communications, Elsevier Science, Amsterdam, NL, vol. 8, No. 9, Jul. 21, 2007, pp. 1349-1353.
Tsuneki, Hideaki, et al., "Deactivation and Regeneration of Ethylenimine Production Catalyst"Applied Catalysis A: General 331 (2007) pp. 95-99.
Waldmann et al., "Uber die Dehydratisierung . . . "Chemische Berichte, 1950, pp. 287-291.
Zhukov et al., "Definition of an Effective Catalyst in the Condensation of Glycerol", Applied Chemistry of USSR, Apr. 1980, pp. 780-783.
CN 2010800573893 Search Report, Nov. 7, 2013, Battalle Memorial Institute.

MULTIHYDRIC COMPOUND DEHYDRATION SYSTEMS, CATALYST
COMPOSITIONS, AND METHODS

CROSS-REFERENCE TO RELATED APPLICATION

This application is a continuation of U.S. patent application Ser. No. 12/973,518 which was filed Dec. 20, 2010, entitled "Multihydric Compound Dehydration Systems, Catalyst Compositions, and Methods", which claims priority to U.S. Provisional Patent Application Ser. No. 61/288,158 which was filed on Dec. 18, 2009, the entirety of each of which is incorporated by reference herein.

TECHNICAL FIELD

The present disclosure relates to chemical production facilities and methods for producing chemicals. More particularly, the present disclosure provides systems and methods for the dehydration of multihydric compounds such as glycerol.

BACKGROUND

Chemical production processes and/or systems can have various attributes that may be desirable or undesirable. For example, a process or system may demonstrate relatively good conversion, in that a substantial amount of the reactant is converted. A process or system may demonstrate relatively good selectivity, in that a substantial amount of the product is the desired product. Further the process or system may prove to be robust, in that relatively good conversions and/or selectivities can be achieved over relatively long periods of time without consuming or damaging process or system infrastructure such as reactors, conduit, or catalysts.

With reference to glycerol dehydration as an example, it is desirable to utilize a process or system for dehydrating glycerol to acrolein that would provide a substantial conversion of glycerol to acrolein without frequently shutting down the process or system for the purpose of replacing and/or refurbishing the process or system infrastructure. Utilizing multihydric reactants such as glycerol in production processes can make obtaining a continuous process difficult for at least the reason that the reactant and product can include multiple reactive sites.

Having to replace or refurbish infrastructure utilized in chemical processing can be costly from a safety perspective as well as a financial perspective. From a safety perspective, it is undesirable that chemical facility operators be required to replace or refurbish reactors, conduits, and/or catalysts for at least the reason that the replacement or refurbishment of these facilities can expose the operator to toxic chemicals and/or hazardous situations.

Further, stopping a system during operation is far from the most cost effective process for economically producing a desired product. It is desirable that facility systems and/or processes operate continuously and/or at a steady state. Under most economic models, continuous supply of reagent to a system without shutting the system down provides the most profitable method for production.

The present disclosure provides facilities, systems, methods, and catalyst compositions that can be utilized in the production of chemical compositions such as acrolein.

SUMMARY

Production facilities for conducting chemically synthetic dehydration processes are provided. According to example implementations, the facilities can include a reaction zone coupled to both a reactant reservoir and a product reservoir, with the reaction zone containing a phosphorous-comprising catalyst, and the facility configured to cyclically produce dehydration product and regenerate the reaction zone, the production of the dehydration product comprising exposing reactant from the reactant reservoir to the catalyst within the reaction zone to form the dehydration product at a production rate, and the regenerating the reaction zone comprising returning the reaction zone to produce the dehydration product at a rate of at least 70% of the production rate.

Chemically synthetic dehydration processes are provided that can include: exposing a multihydric reactant to a dehydration catalyst within a reactor to form a dehydration product; ceasing the providing of the reactant to the reactor; after ceasing the providing of the reactant, providing a gas to the reactor while maintaining the temperature of the catalyst below 800° C.; and after providing the gas, again providing reactant to the reactor.

Chemically synthetic dehydration processes can also include: exposing an aqueous reactant mixture to a dehydration catalyst within a reactor to form a dehydration product, the reactant mixture comprising water and a multihydric reactant; ceasing the providing of the multihydric reactant to the reactor; after ceasing the providing of the multihydric reactant, providing gaseous water to the reactor; and again exposing the reactant mixture to the reactor.

Chemically synthetic dehydration processes can also include: providing glycerol to a reactor having a dehydration catalyst therein, the catalyst transforming at least a portion of glycerol to a dehydration product; ceasing the providing of the glycerol to the reactor; after ceasing the providing of the glycerol, providing an oxidizing reagent to the reactor while maintaining the temperature of the catalyst below 800° C.; and after providing the reagent, again providing glycerol to the reactor.

Chemically synthetic dehydration processes can also include: providing a dehydration catalyst within a reactor; providing glycerol to the reactor via a first conduit; providing water to the reactor via a second conduit; exposing the catalyst to the glycerol to form a dehydration product; ceasing the exposing of the catalyst to the glycerol; after the ceasing of the exposing of the catalyst to the glycerol, exposing the catalyst to the water, wherein the water is in primarily the gaseous form; and after exposing the gaseous water to the catalyst, providing glycerol to the reactor to form a dehydration product.

Chemically synthetic dehydration processes can include: providing a reactor having a dehydration catalyst bed therein; exposing glycerol to the catalyst bed to form a dehydration product from the glycerol; forming carbon by-products within the reactor; ceasing the providing of the glycerol to the catalyst bed; after the ceasing, exposing the reactor to a gas, and heating the contents of the reactor to a temperature sufficient to release at least a portion of the carbon by-products from the reactor; and after the heating of the contents of the reactor, again providing glycerol to within the reactor. Glycerol dehydration catalysts are provided that can include a fumed support material; phosphate; and at least one or more metals from groups 2-12 of the periodic table and/or Rb, K, and Cs.

Glycerol dehydration methods are provided that can include exposing glycerol to a catalyst, with the catalyst comprising a fumed support material, phosphate, and at least one or more metals from groups 2-12 of the periodic table and/or Rb, K, and Cs, the exposing forming one or both of acrolein and acetol.

Glycerol dehydration catalyst regeneration methods are provided that can include: providing a used glycerol dehydration catalyst, the catalyst comprising a fumed support material, phosphate, and at least one or more metals from groups 2-12 of the periodic table and/or Rb, K, and Cs; and exposing the used catalyst to either $N_2$ alone or air while maintaining a temperature of the catalyst above 200° C. to remove carbon from the used catalyst.

Glycerol dehydration systems are provided that can include: a reactor coupled to at least two conduits, one of the two conduits configured to convey reactants to the reactor, and the other of the two conduits configured to convey products from the reactor; a catalyst within the reactor, the catalyst comprising a fumed support material, phosphate, and at least one or more metals from groups 2-12 of the periodic table and/or Rb.

Chemically synthetic dehydration processes are provided that can include exposing a multihydric reactant to a phosphorous-comprising catalyst within a reactor to form a dehydration product. The processes can further include ceasing the providing of the reactant to the reactor, and, after ceasing the providing of the reactant, providing a phosphorous-comprising material to the reactor, the phosphorous-comprising material increasing the amount of phosphorous in the dehydration catalyst. Processes can also include, after providing the phosphorous-comprising material, again providing reactant to the reactor.

Chemically synthetic dehydration processes are provided that can include exposing a multihydric compound to a Rb-phosphate catalyst to form a dehydration product of the multihydric compound.

DRAWINGS

Embodiments of the disclosure are described below with reference to the following accompanying drawings.

Figure 4:
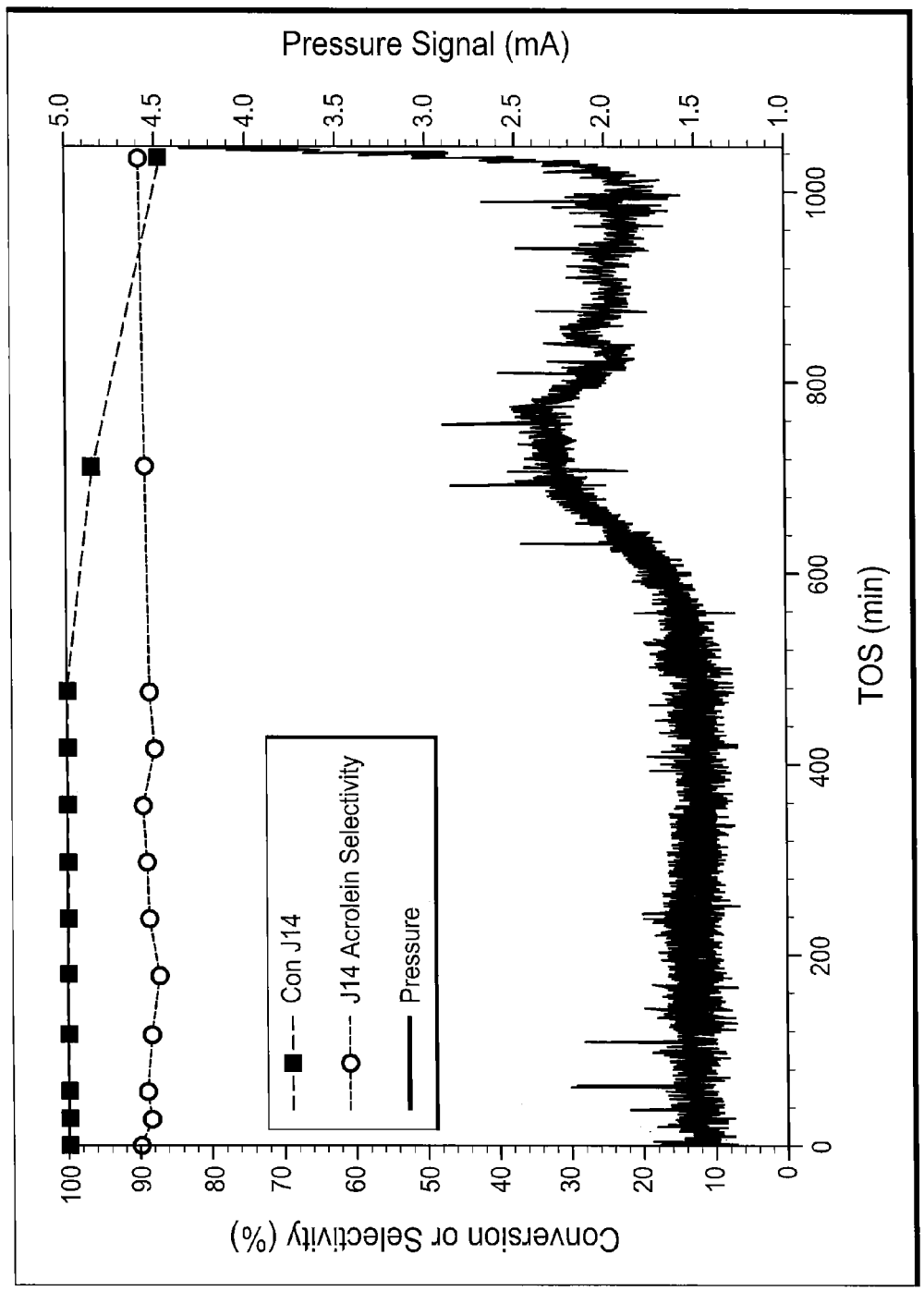
Figure 4A:
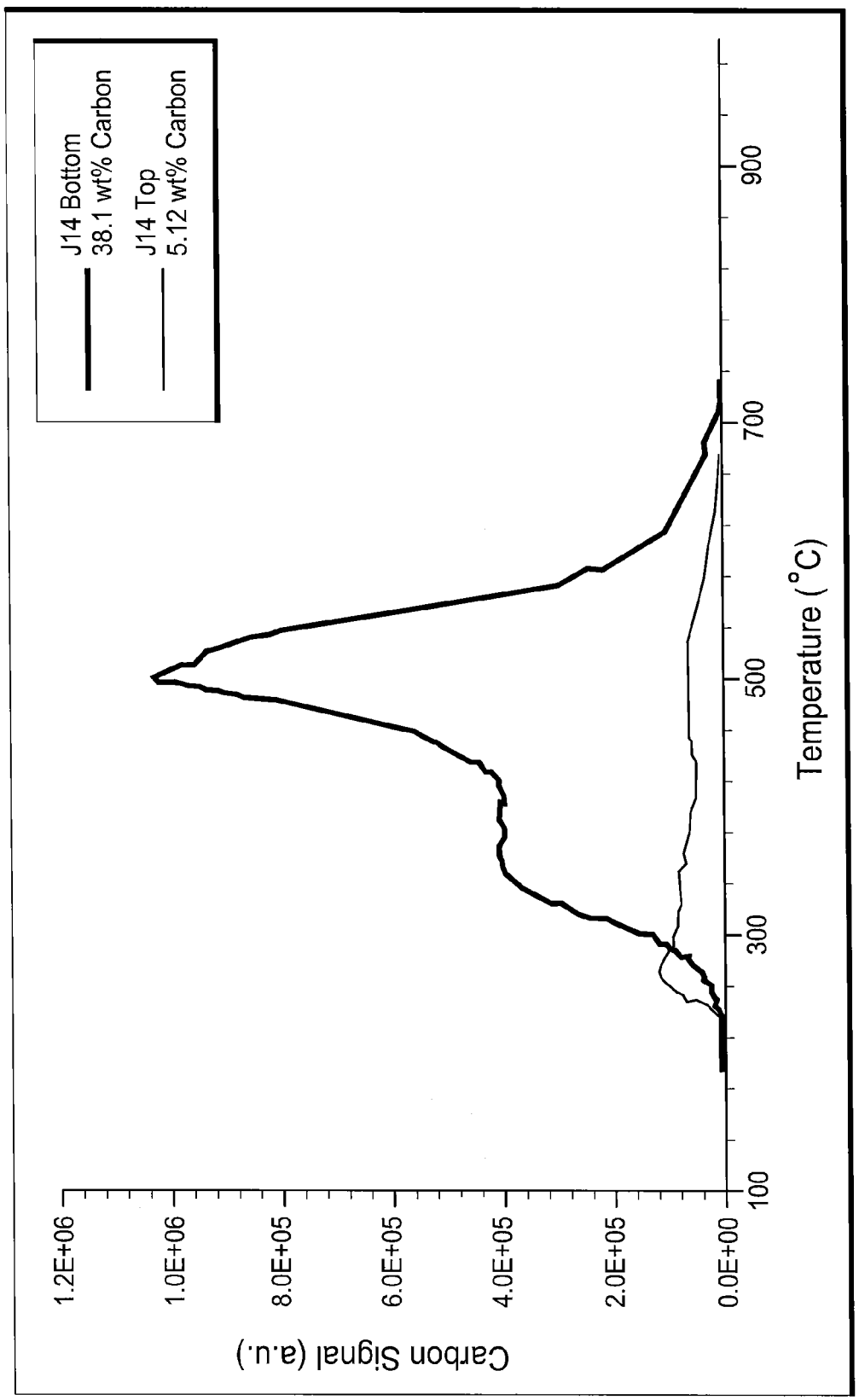
Figure 4B:
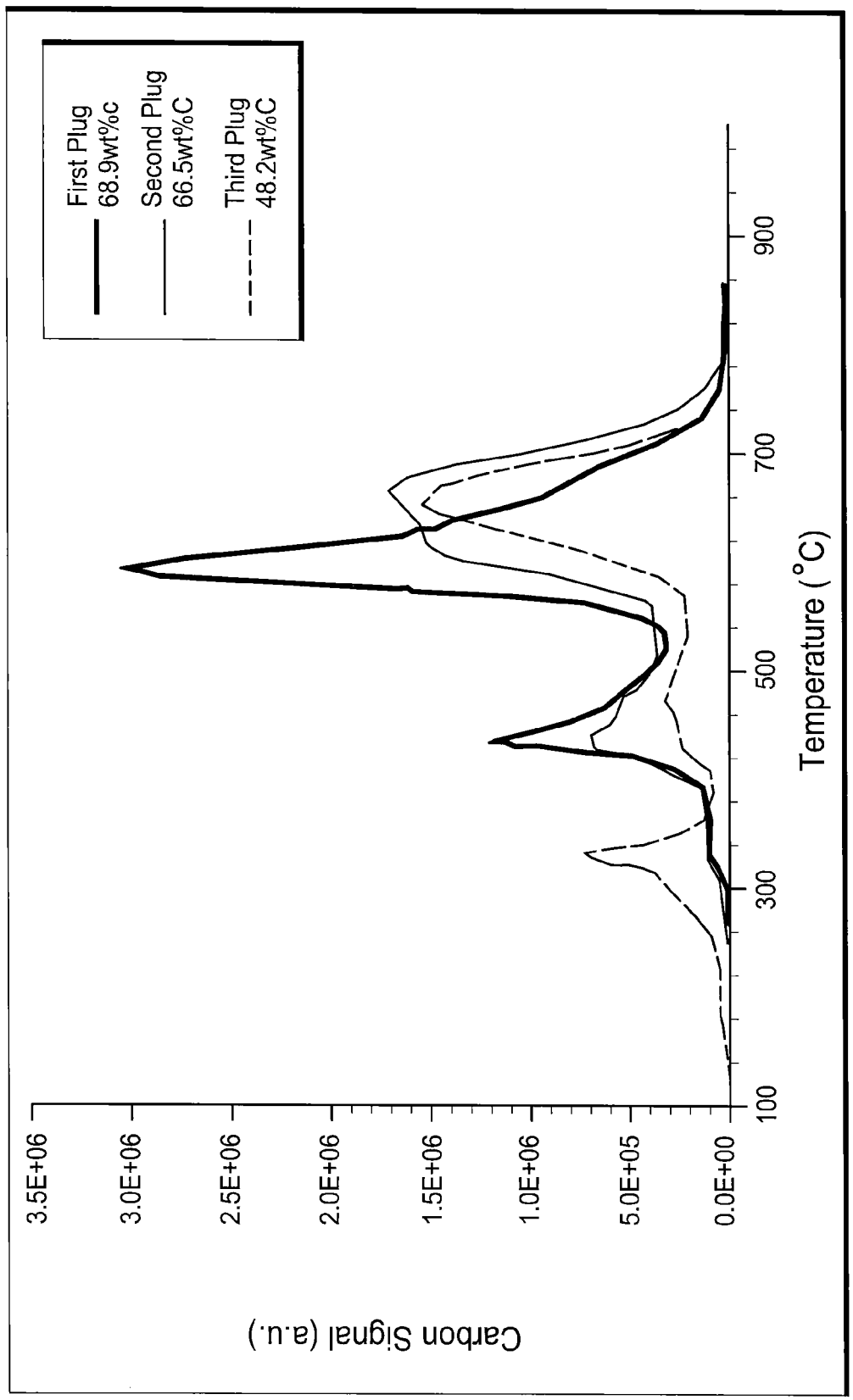

FIGS. 4, 4A, and 4B are plots of data acquired utilizing embodiments of the systems, compositions, and/or methods of the present disclosure.

Figure 5:
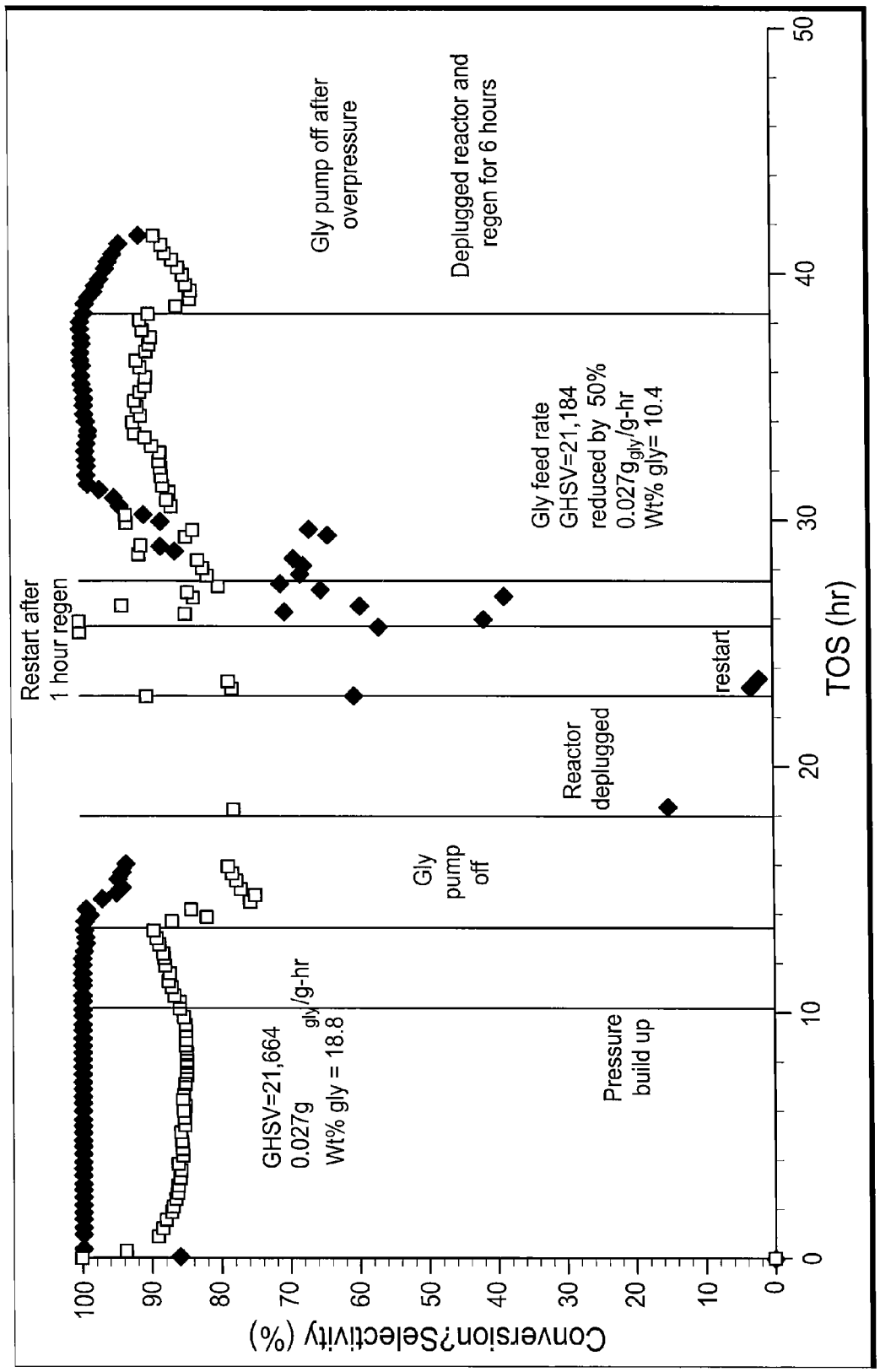

FIG. 5 is a plot of data acquired utilizing embodiments of the systems, compositions, and/or methods of the present disclosure.

Figure 6:
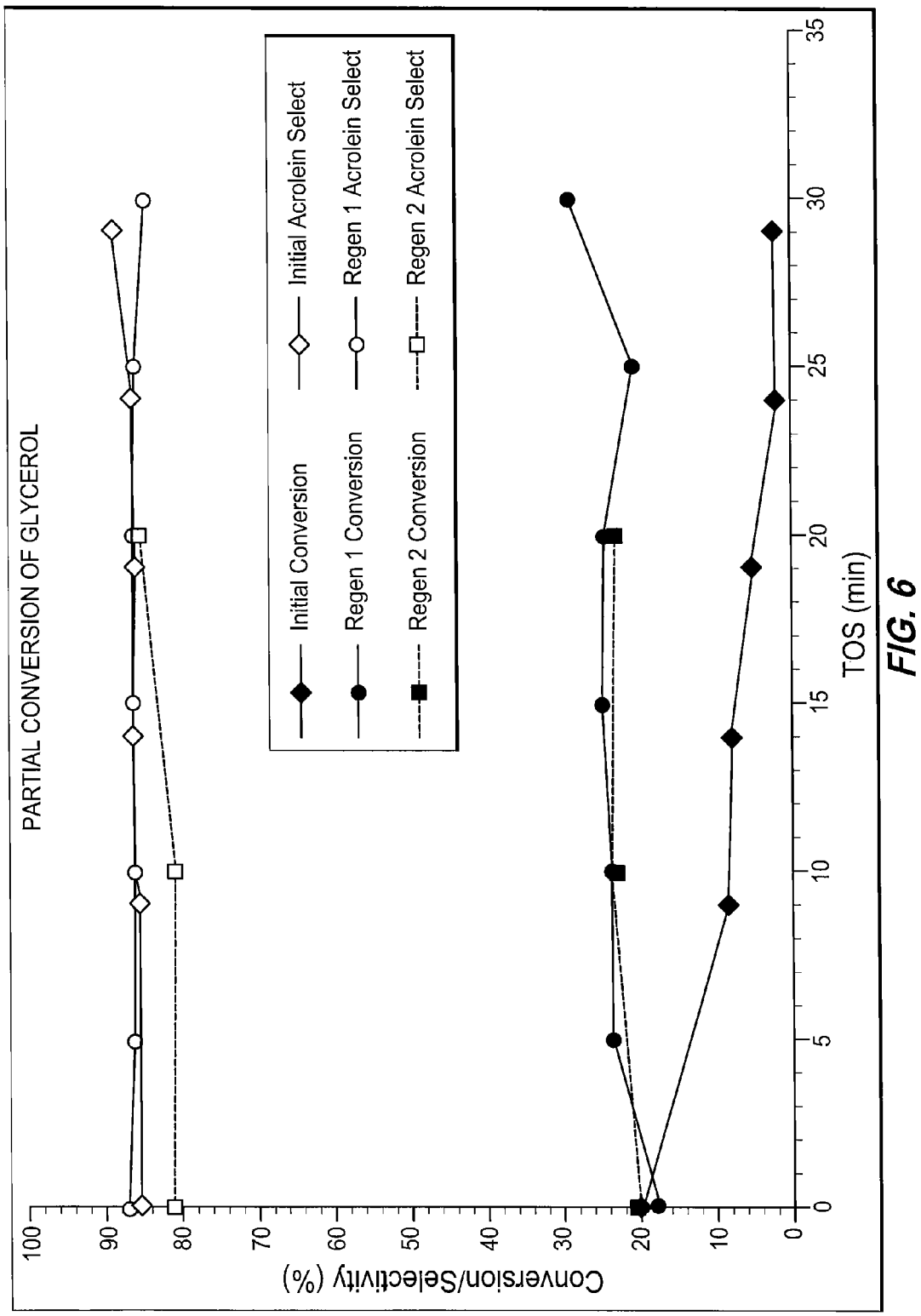

FIG. 6 is a plot of data acquired utilizing embodiments of the systems, compositions, and/or methods of the present disclosure.

Figure 7:
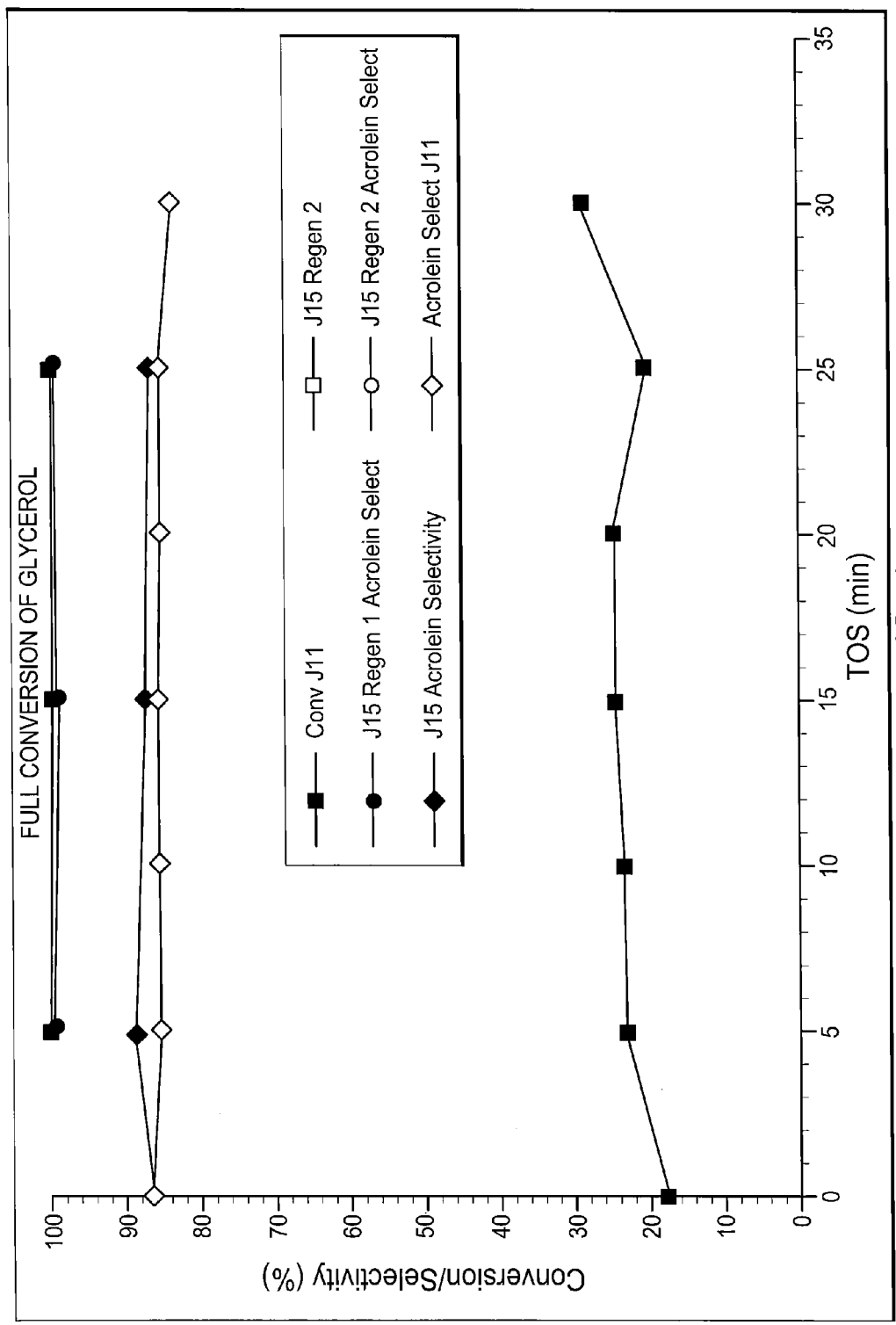

FIG. 7 is a plot of data acquired utilizing embodiments of the systems, compositions, and/or methods of the present disclosure.

Figure 8:
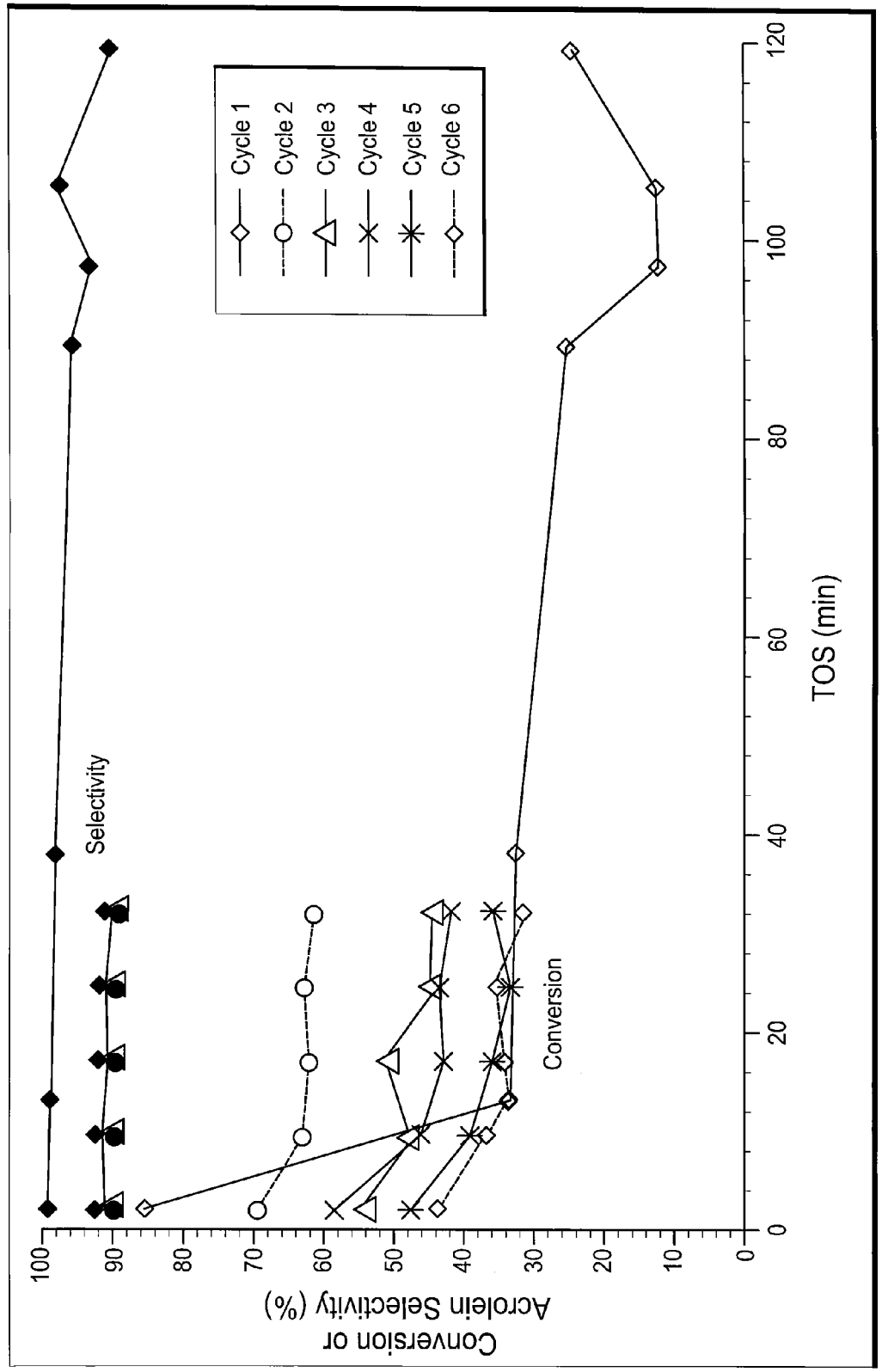

FIG. 8 is a plot of data acquired utilizing embodiments of the systems, compositions, and/or methods of the present disclosure.

Figure 9:
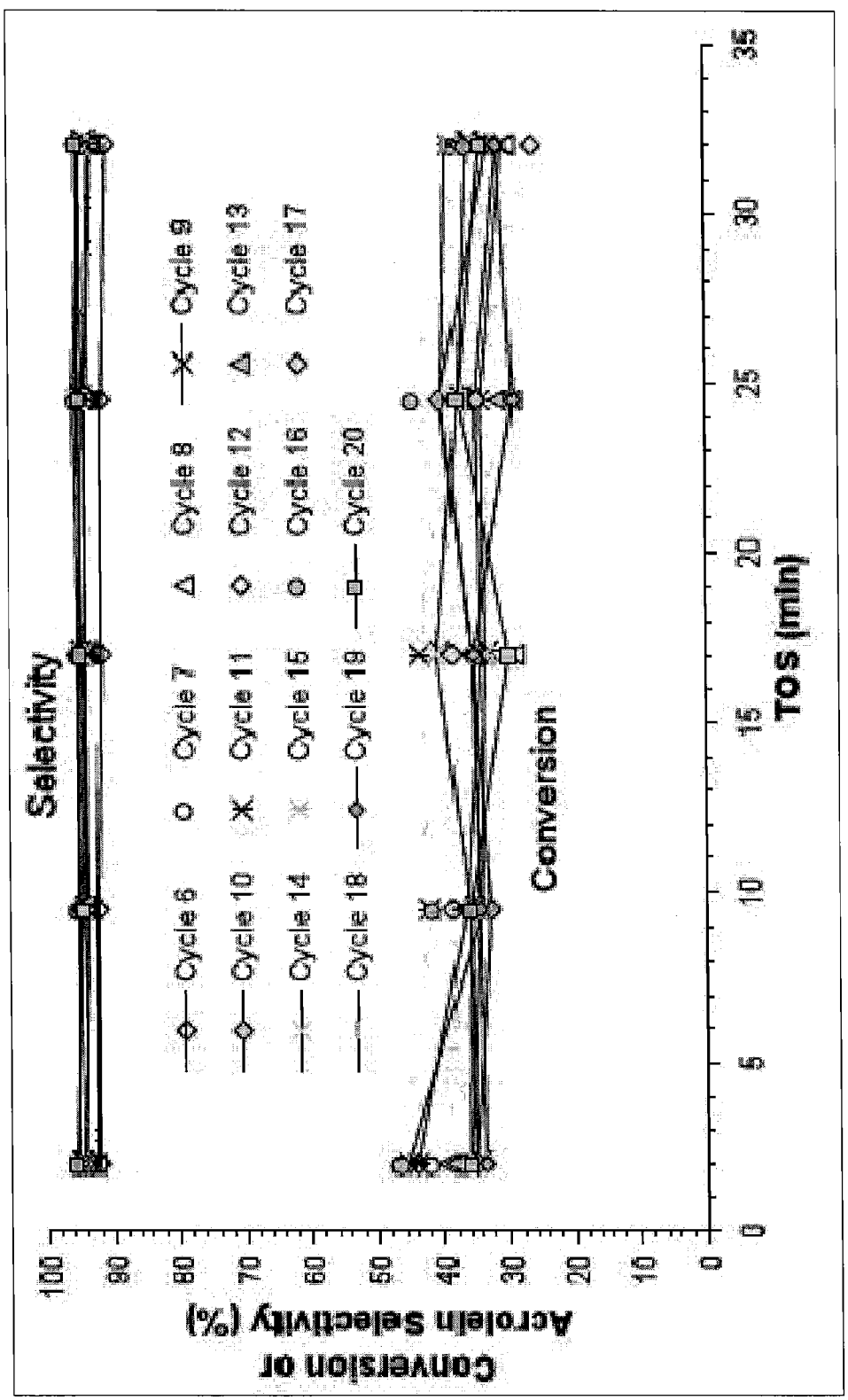

FIG. 9 is a plot of data acquired utilizing embodiments of the systems, compositions, and/or methods of the present disclosure.

Figure 10:
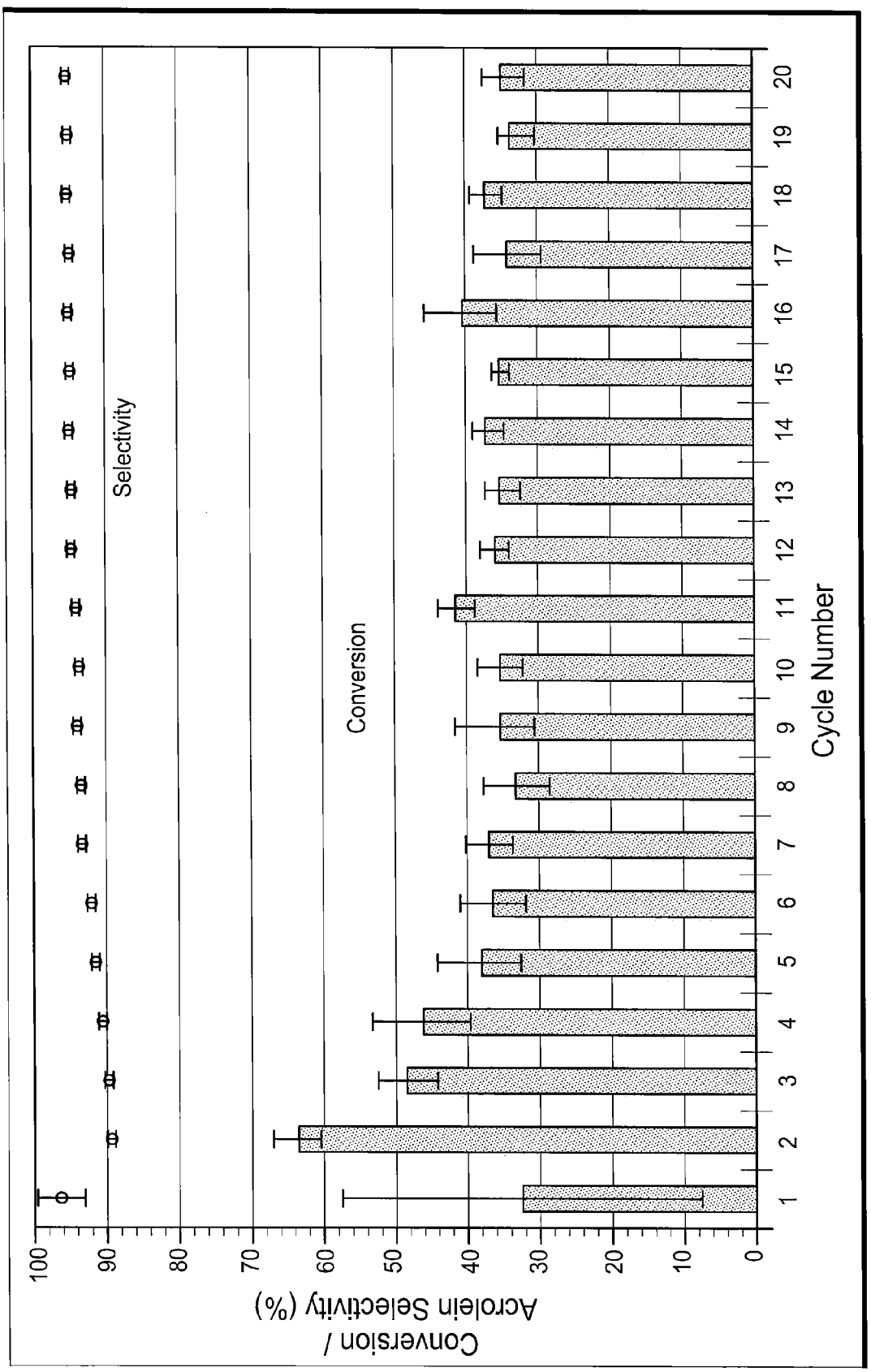

FIG. 10 is a plot of data acquired utilizing embodiments of the systems, compositions, and/or methods of the present disclosure.

Figure 11:
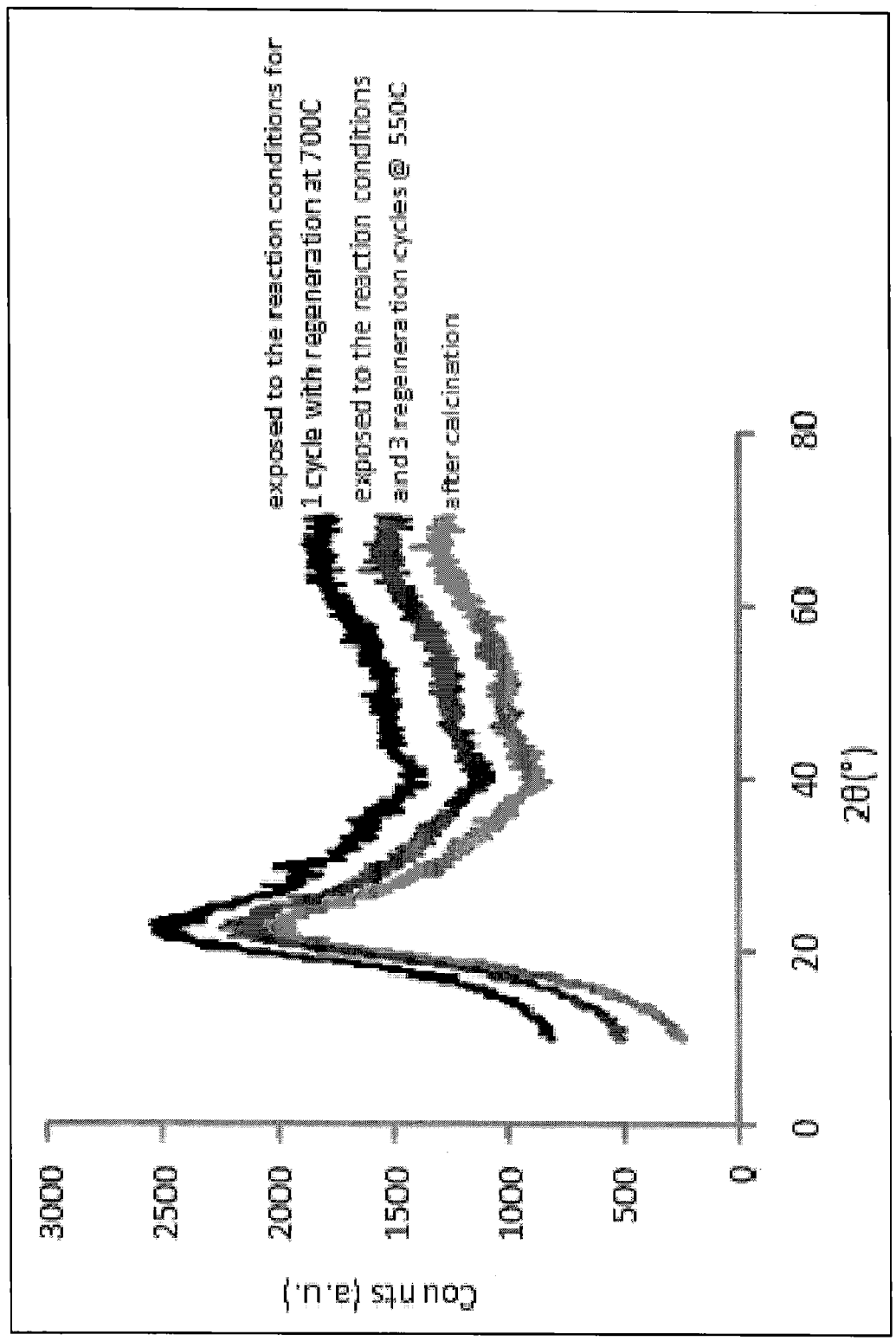

FIG. 11 is a plot of data acquired utilizing embodiments of the systems, compositions, and/or methods of the present disclosure.

Figure 12:
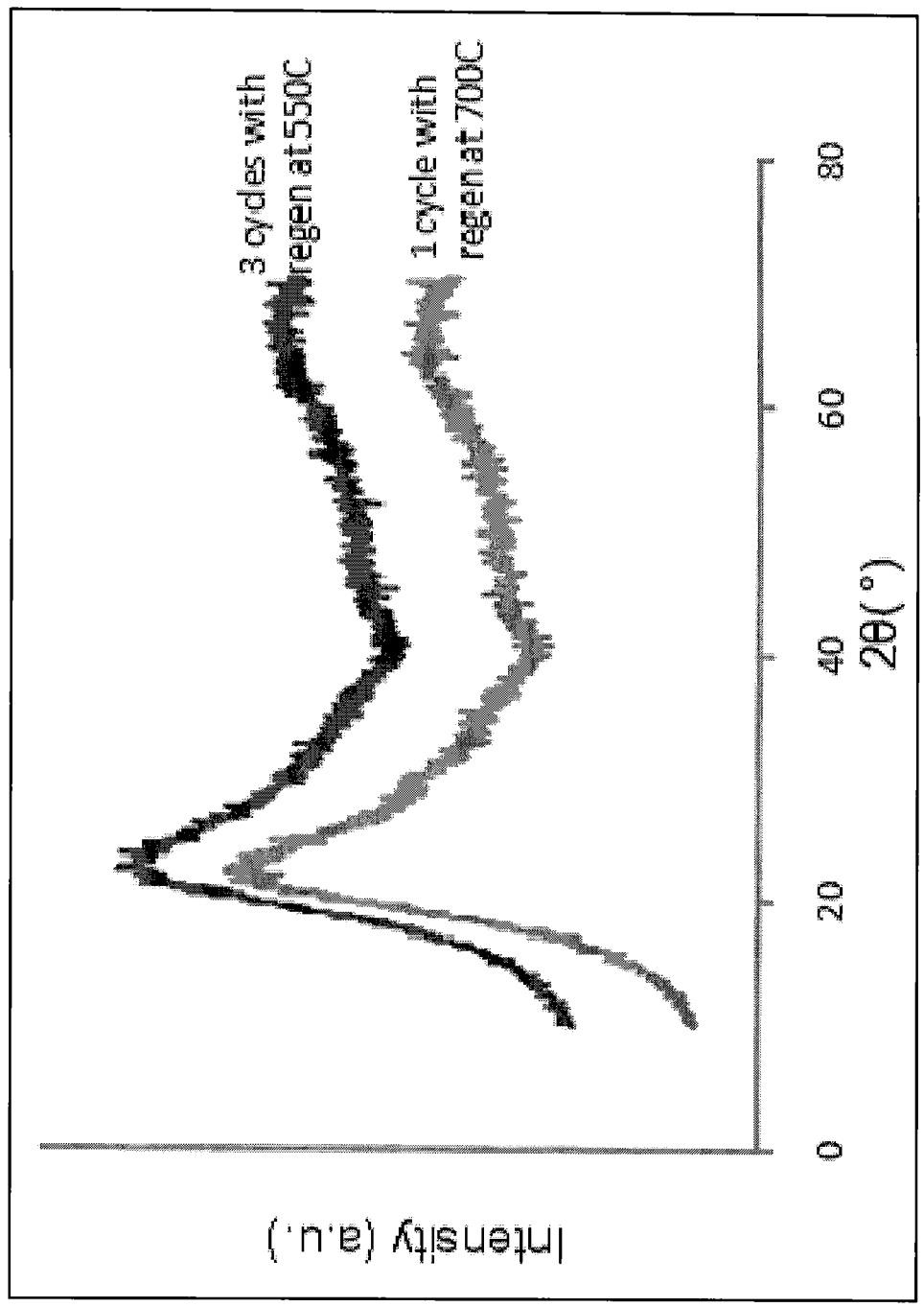

FIG. 12 is a plot of data acquired utilizing embodiments of the systems, compositions, and/or methods of the present disclosure.

Figure 13:
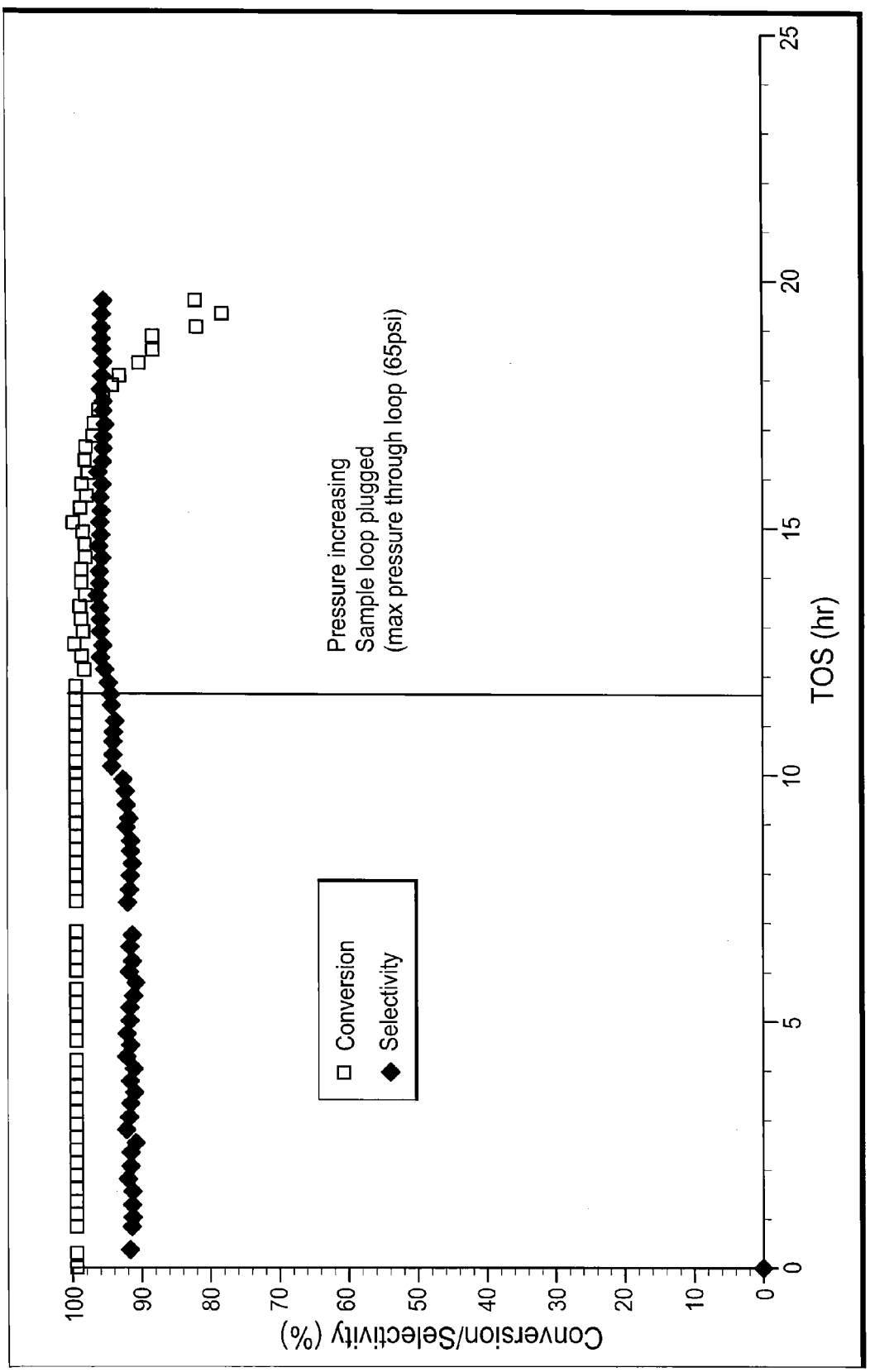

FIG. 13 is a plot of data acquired utilizing embodiments of the systems, compositions, and/or methods of the present disclosure.

Figure 14:
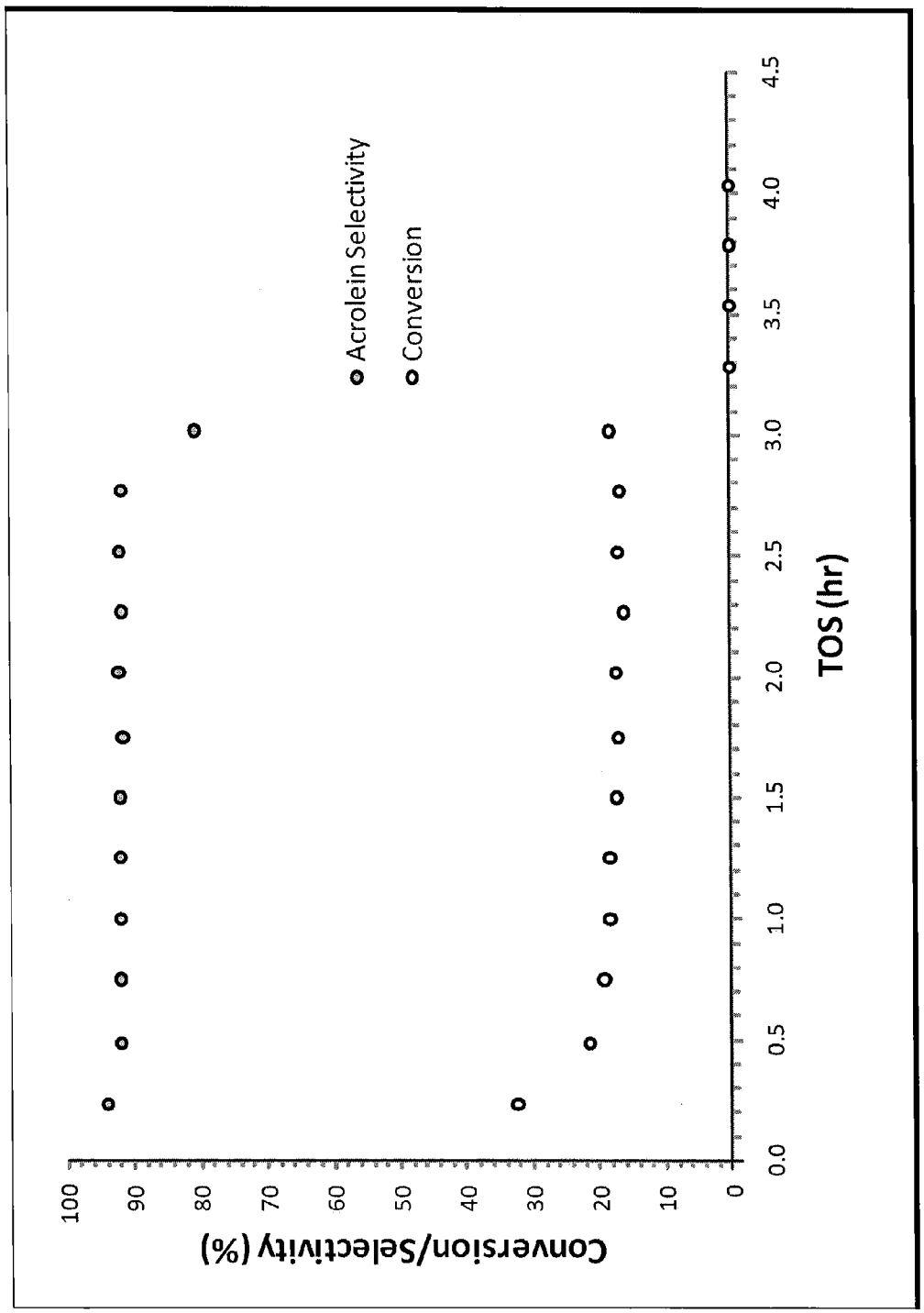

FIG. 14 is a plot of data acquired utilizing embodiments of the systems, compositions, and/or methods of the present disclosure.

Figure 15:
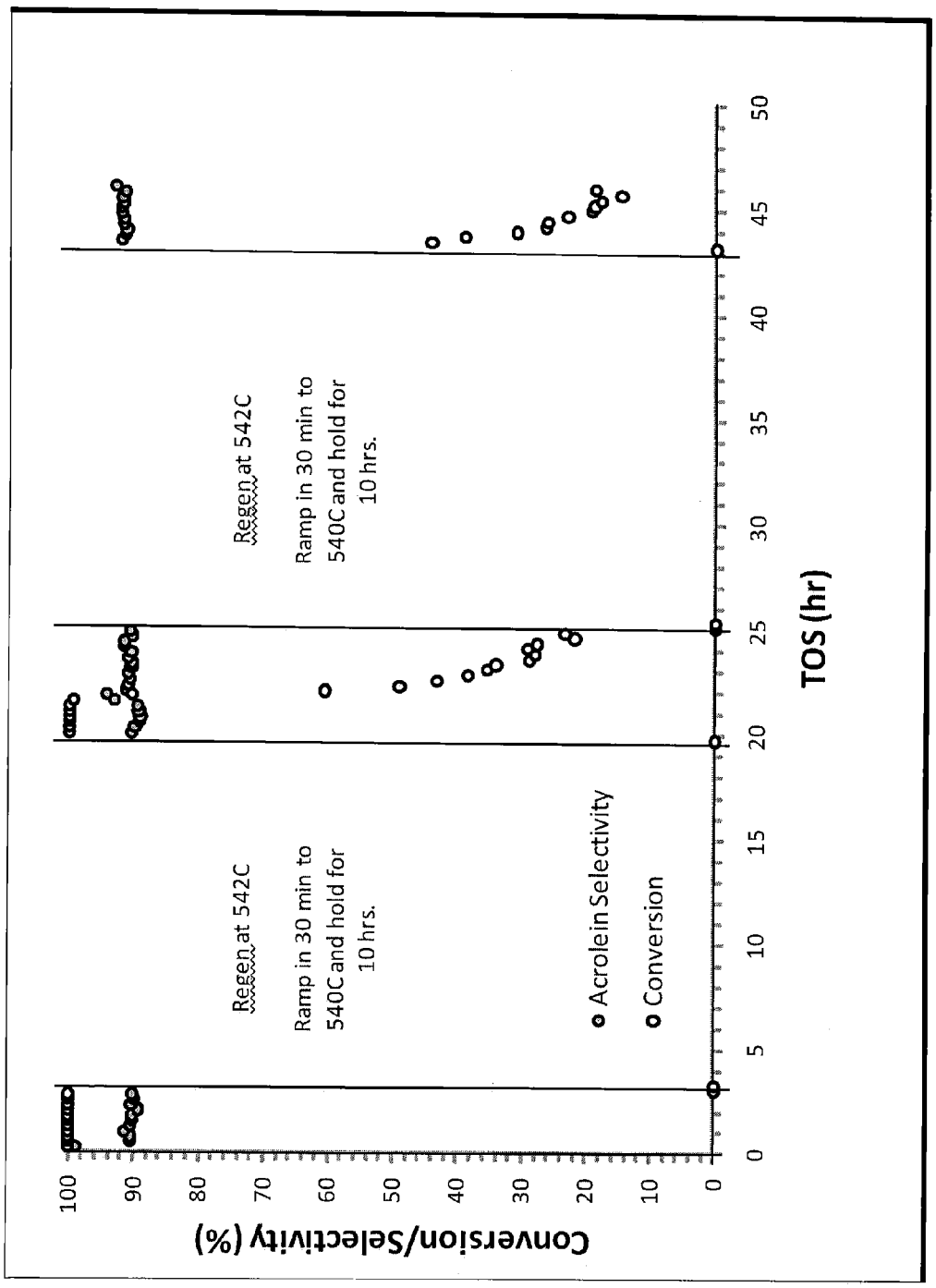

FIG. 15 is a plot of data acquired utilizing embodiments of the systems, compositions, and/or methods of the present disclosure.

Figure 16:
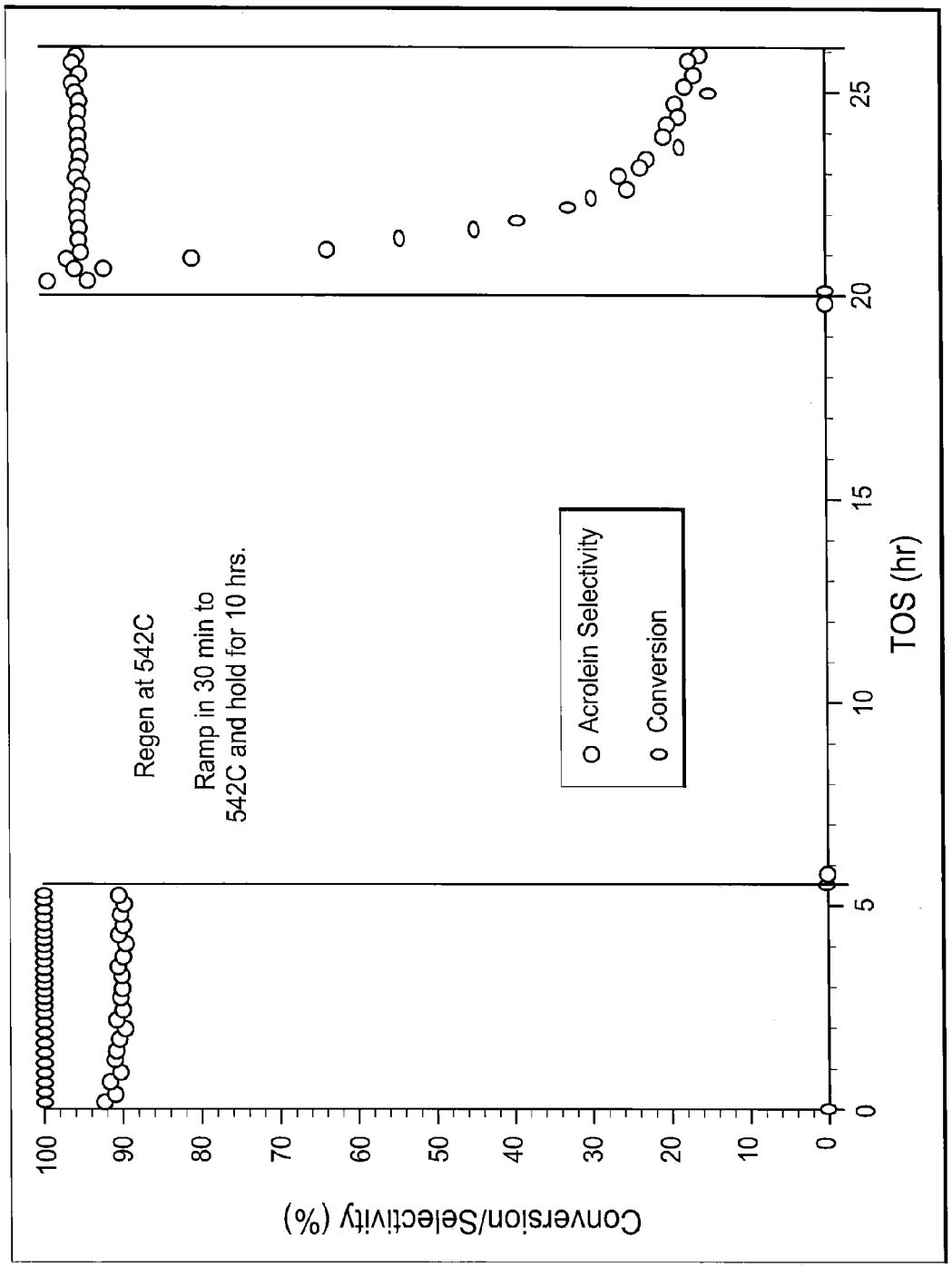

FIG. 16 is a plot of data acquired utilizing embodiments of the systems, compositions, and/or methods of the present disclosure.

Figure 17:
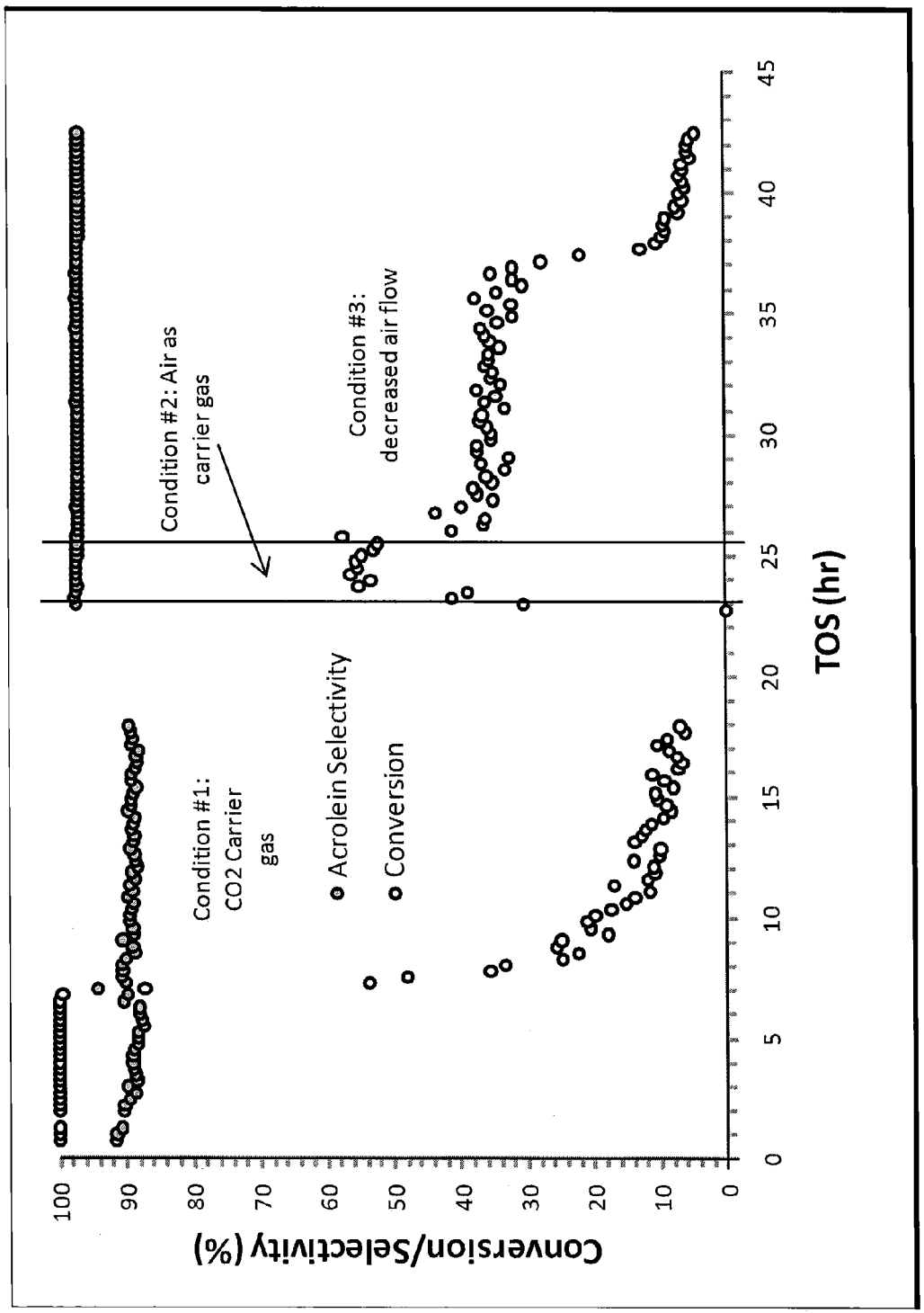

FIG. 17 is a plot of data acquired utilizing embodiments of the systems, compositions, and/or methods of the present disclosure.

Figure 18:
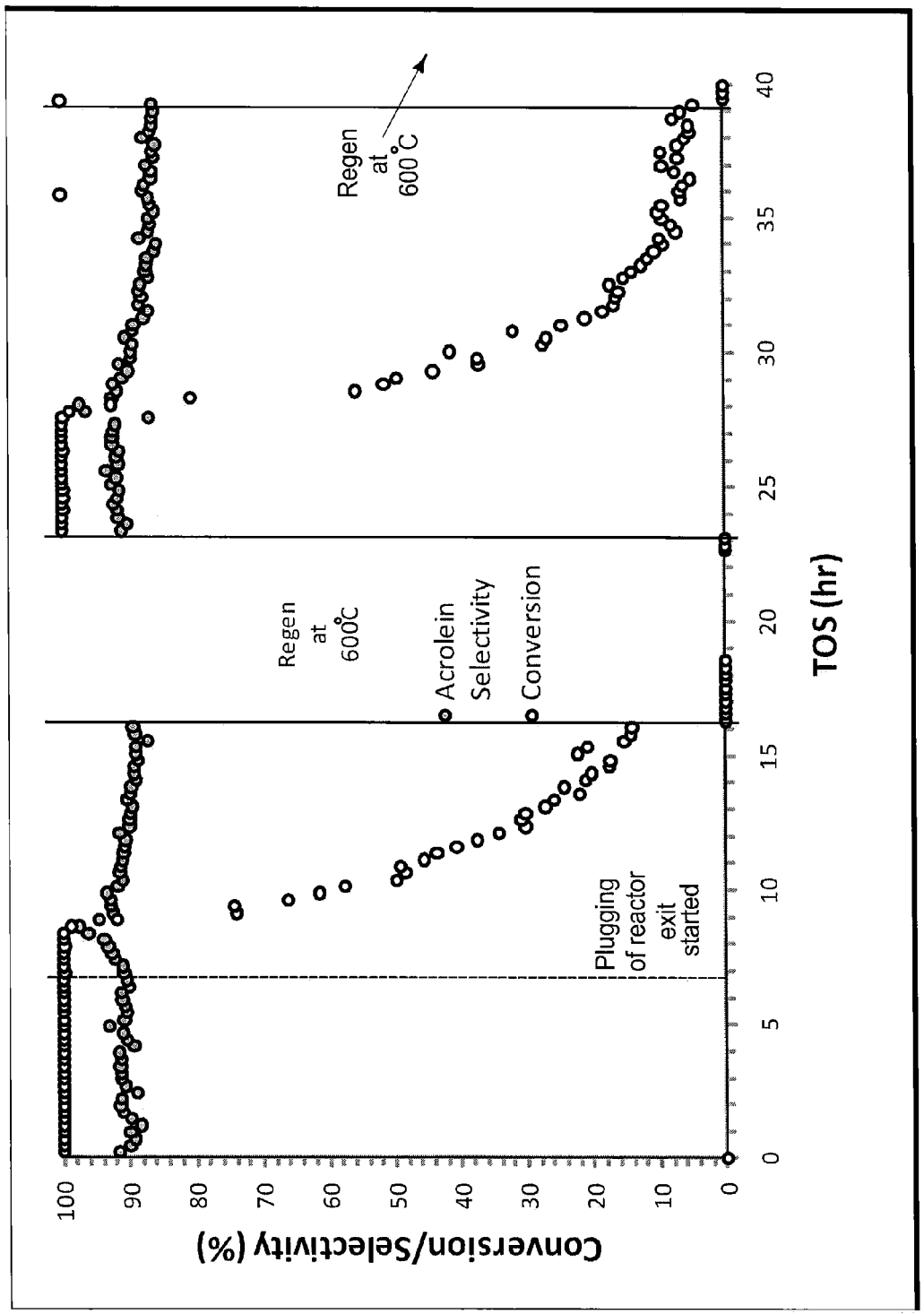

FIG. 18 is a plot of data acquired utilizing embodiments of the systems, compositions, and/or methods of the present disclosure.

Figure 19:
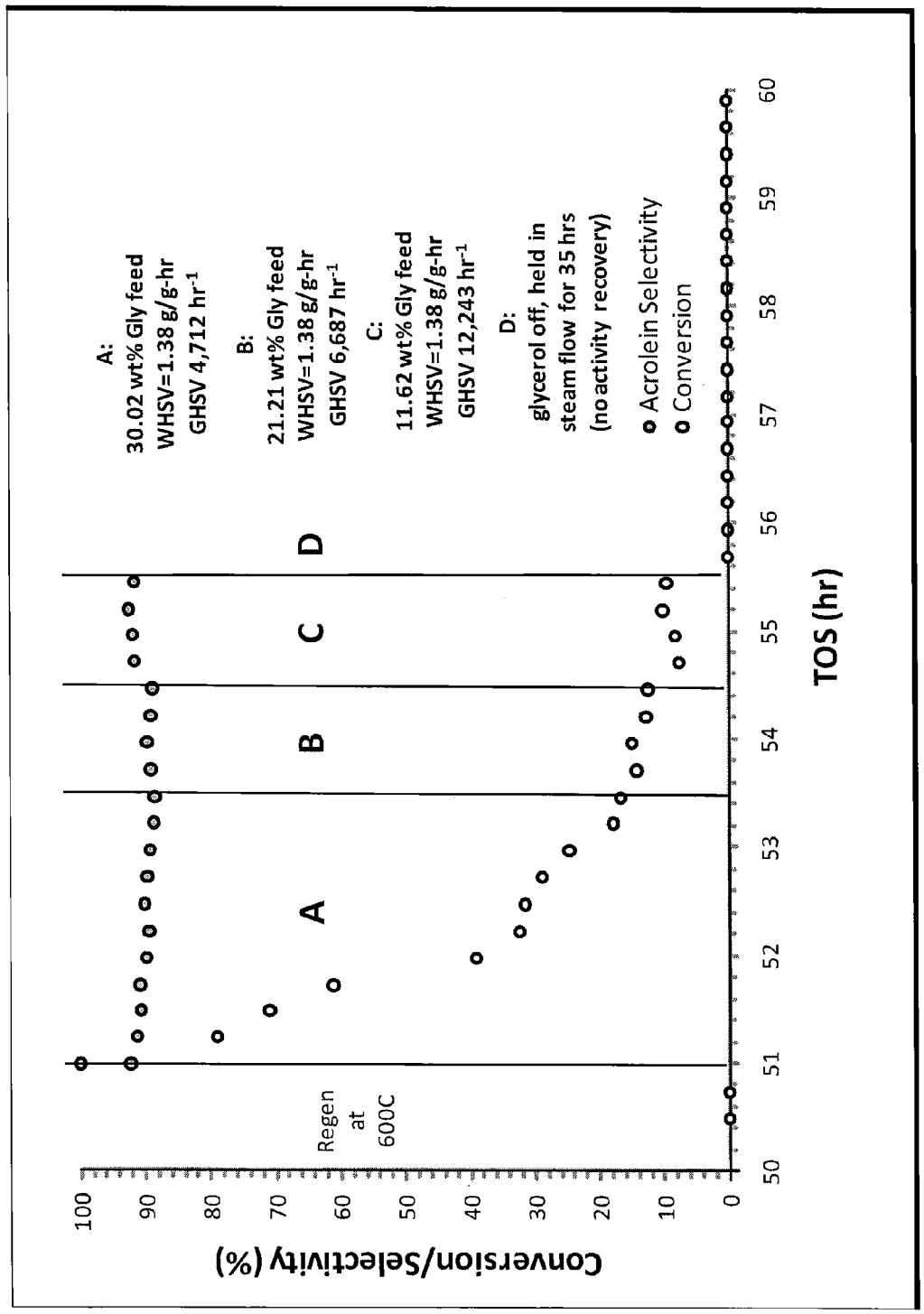

FIG. 19 is a plot of data acquired utilizing embodiments of the systems, compositions, and/or methods of the present disclosure.

Figure 20:
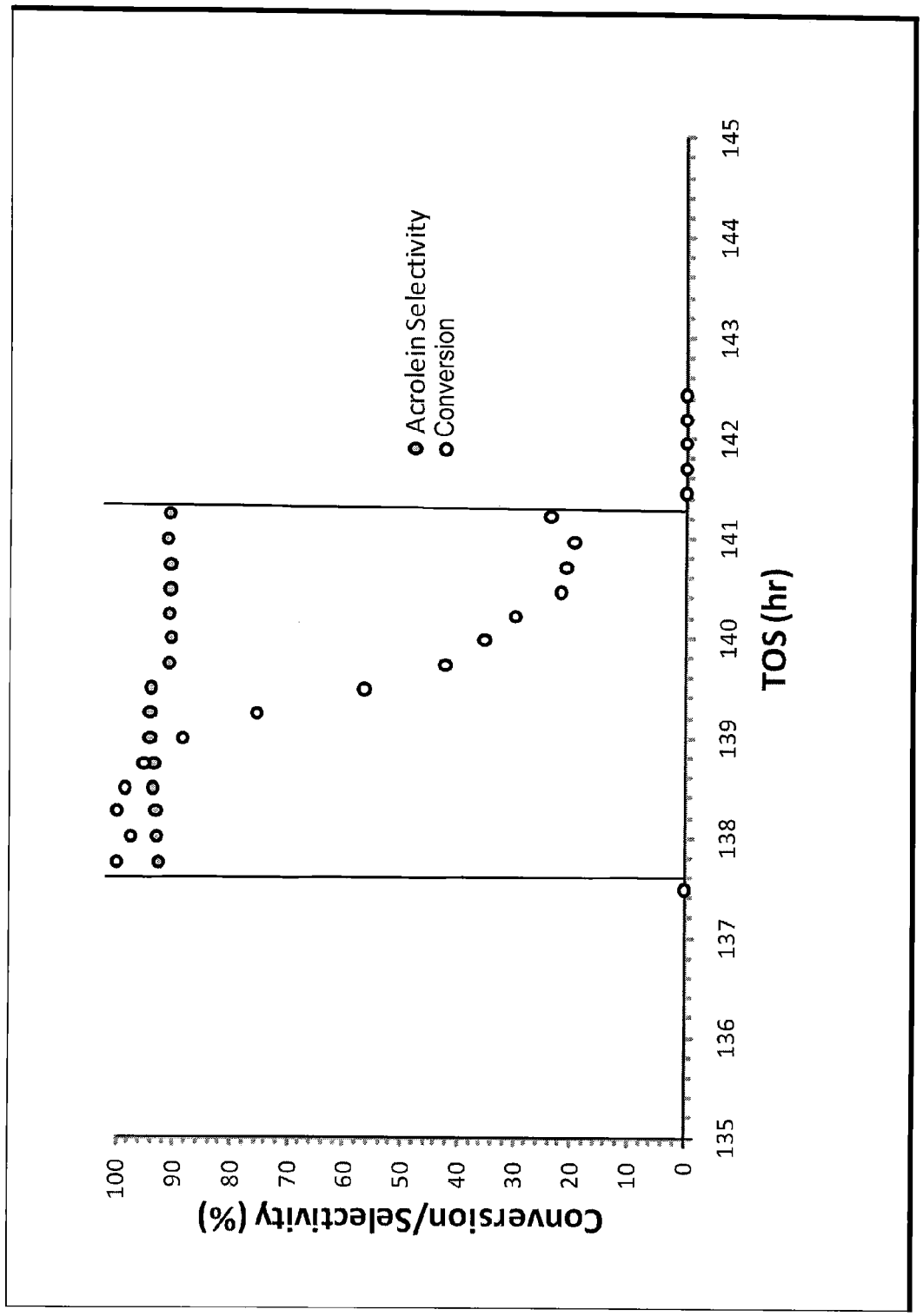

FIG. 20 is a plot of data acquired utilizing embodiments of the systems, compositions, and/or methods of the present disclosure.

Figure 21:
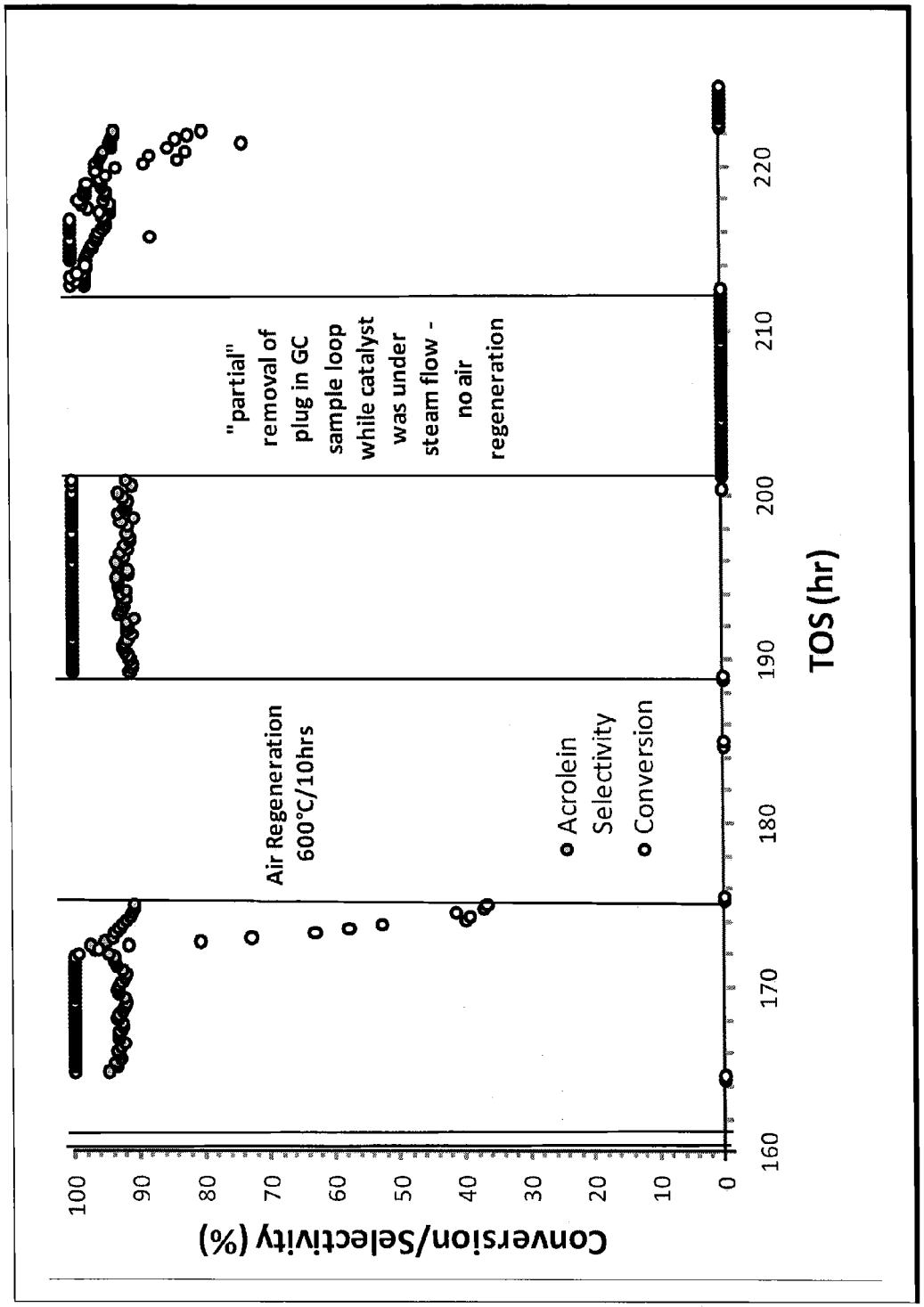

FIG. 21 is a plot of data acquired utilizing embodiments of the systems, compositions, and/or methods of the present disclosure.

Figure 22:
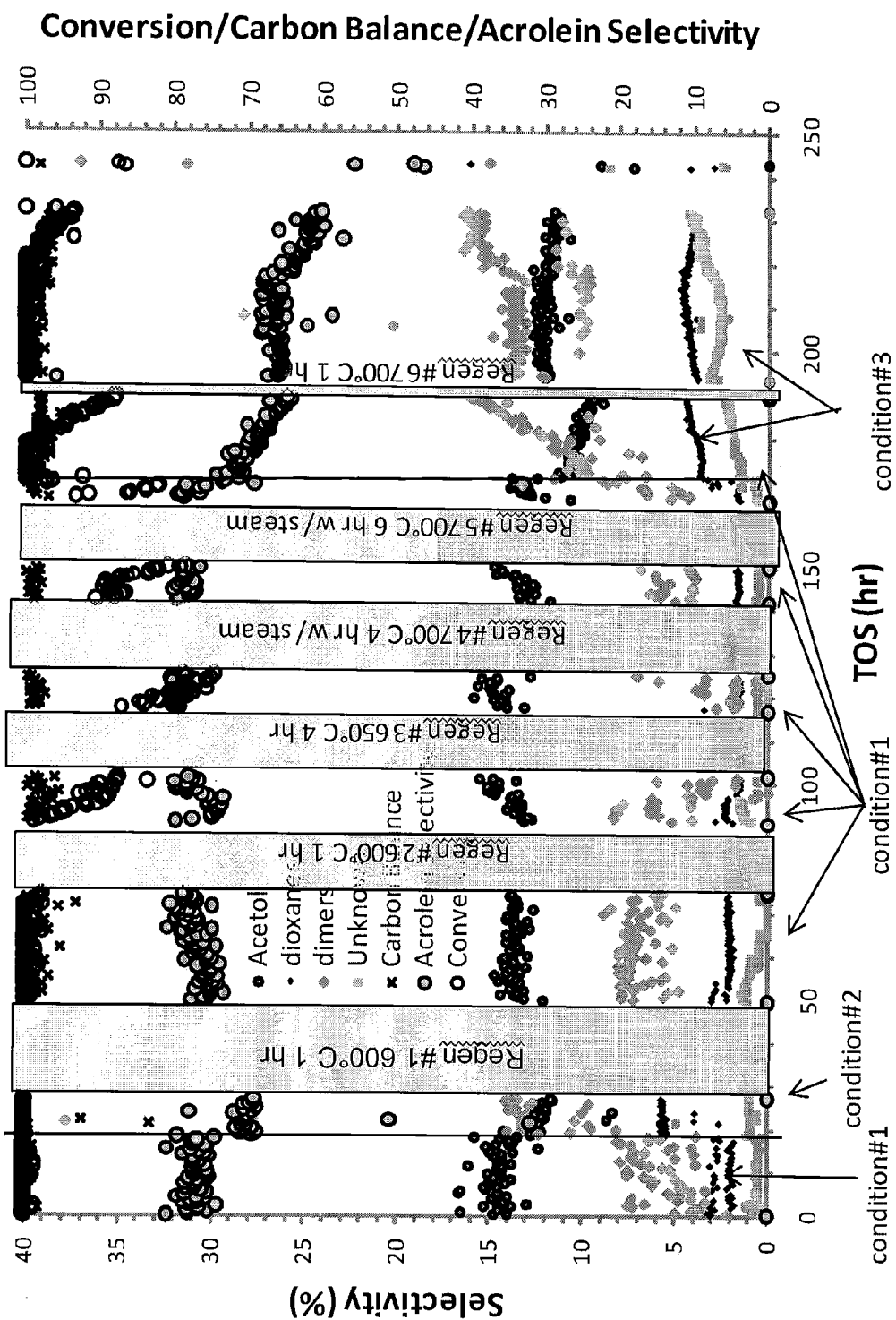

FIG. 22 is a plot of data acquired utilizing embodiments of the systems, compositions, and/or methods of the present disclosure.

Figure 23:
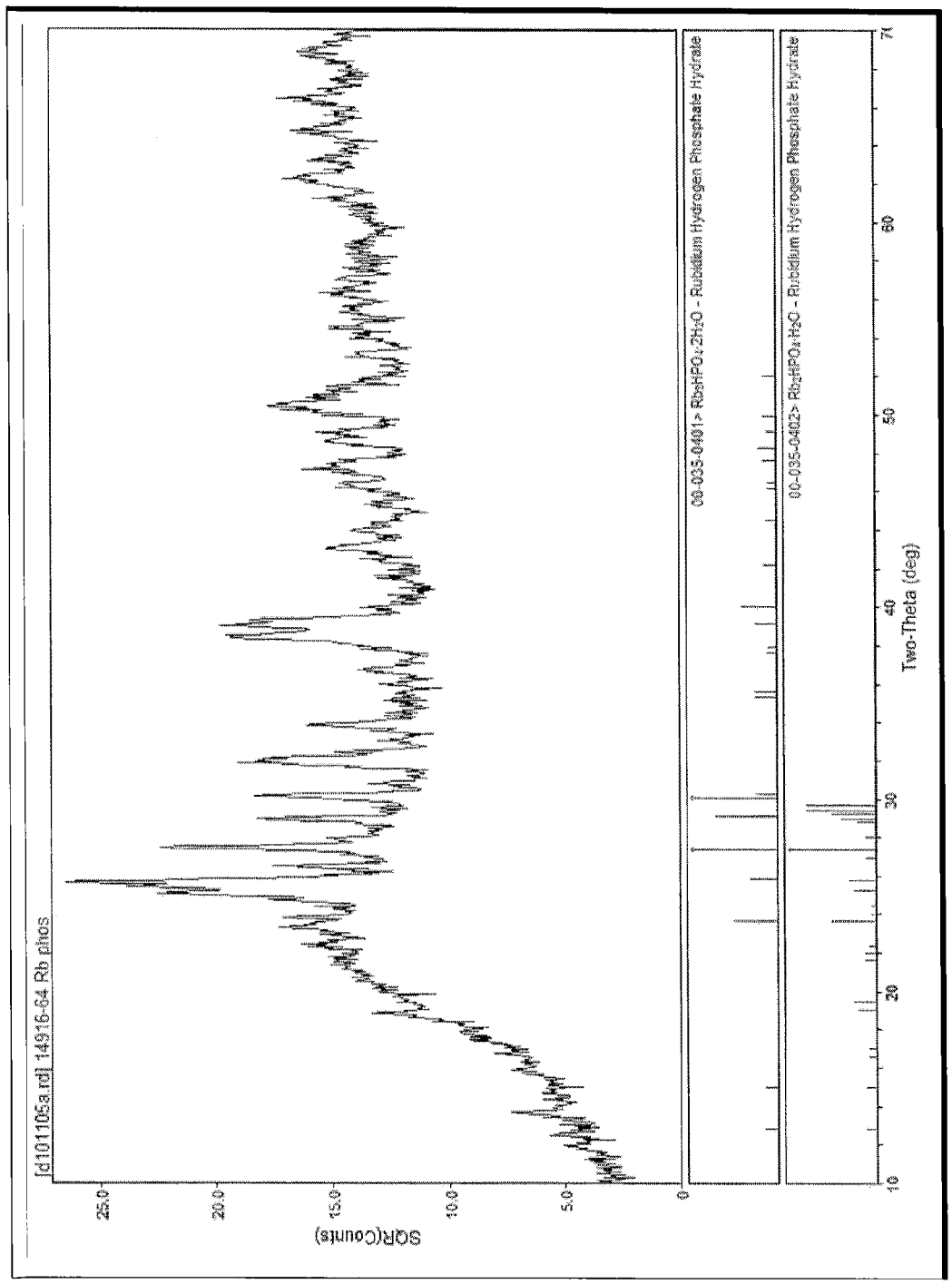

FIG. 23 is a plot of data acquired utilizing embodiments of the systems, compositions, and/or methods of the present disclosure.

Figure 24:
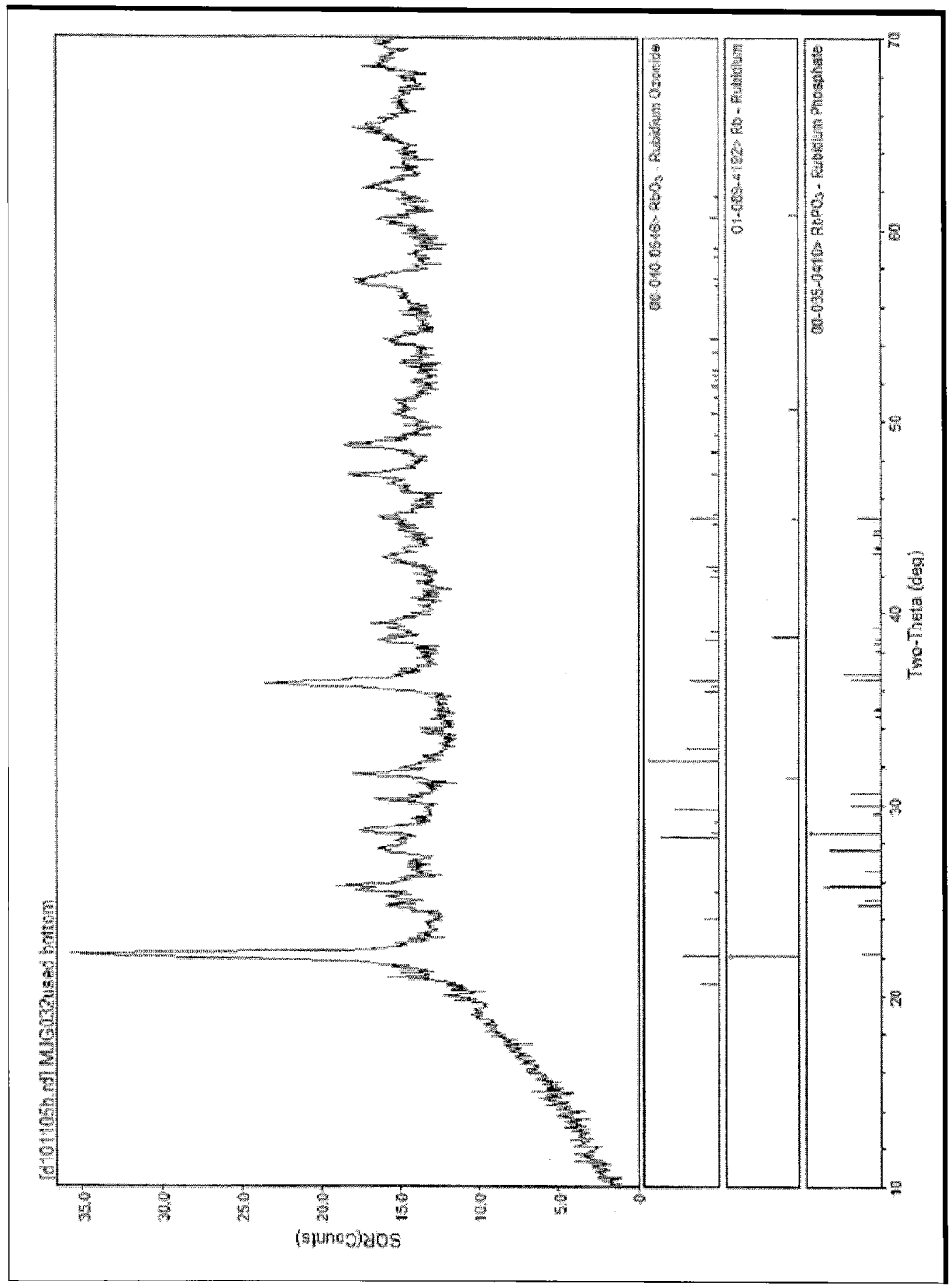

FIG. 24 is a plot of data acquired utilizing embodiments of the systems, compositions, and/or methods of the present disclosure.

Figure 25:
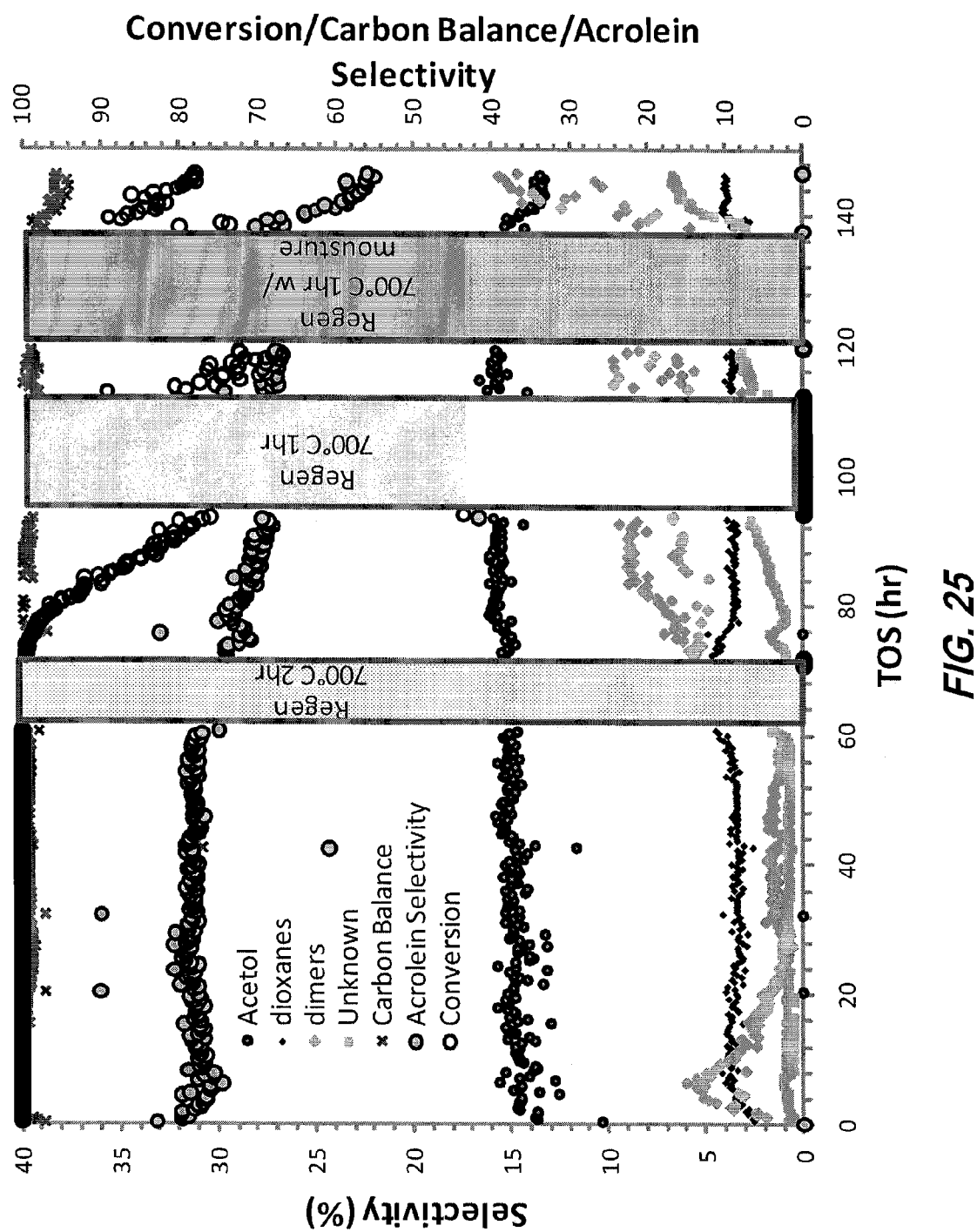

FIG. 25 is a plot of data acquired utilizing embodiments of the systems, compositions, and/or methods of the present disclosure.

Figure 26:
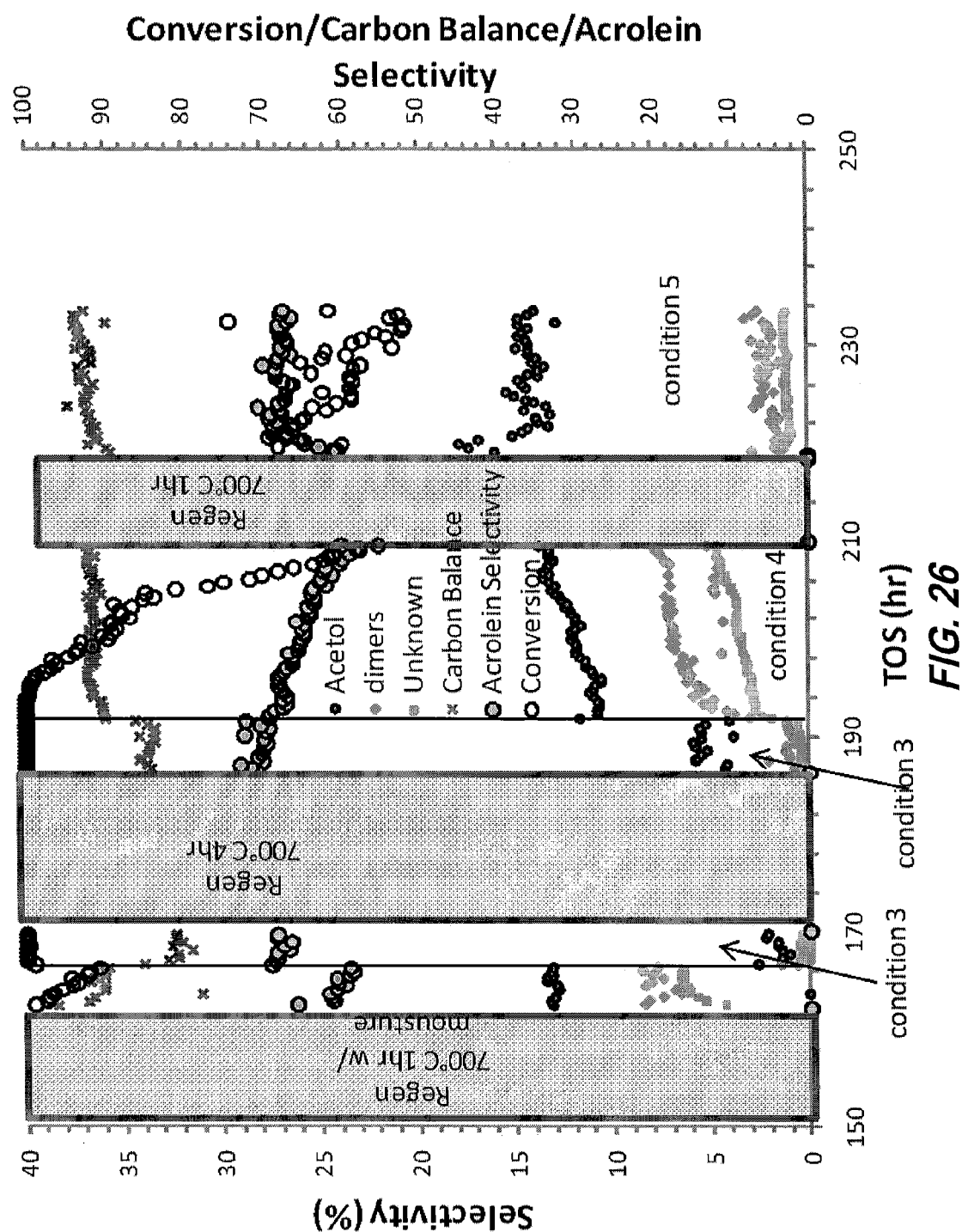

FIG. 26 is a plot of data acquired utilizing embodiments of the systems, compositions, and/or methods of the present disclosure.

DESCRIPTION

This disclosure is submitted in furtherance of the constitutional purposes of the U.S. Patent Laws "to promote the progress of science and useful arts" (Article 1, Section 8).

Figure 1:
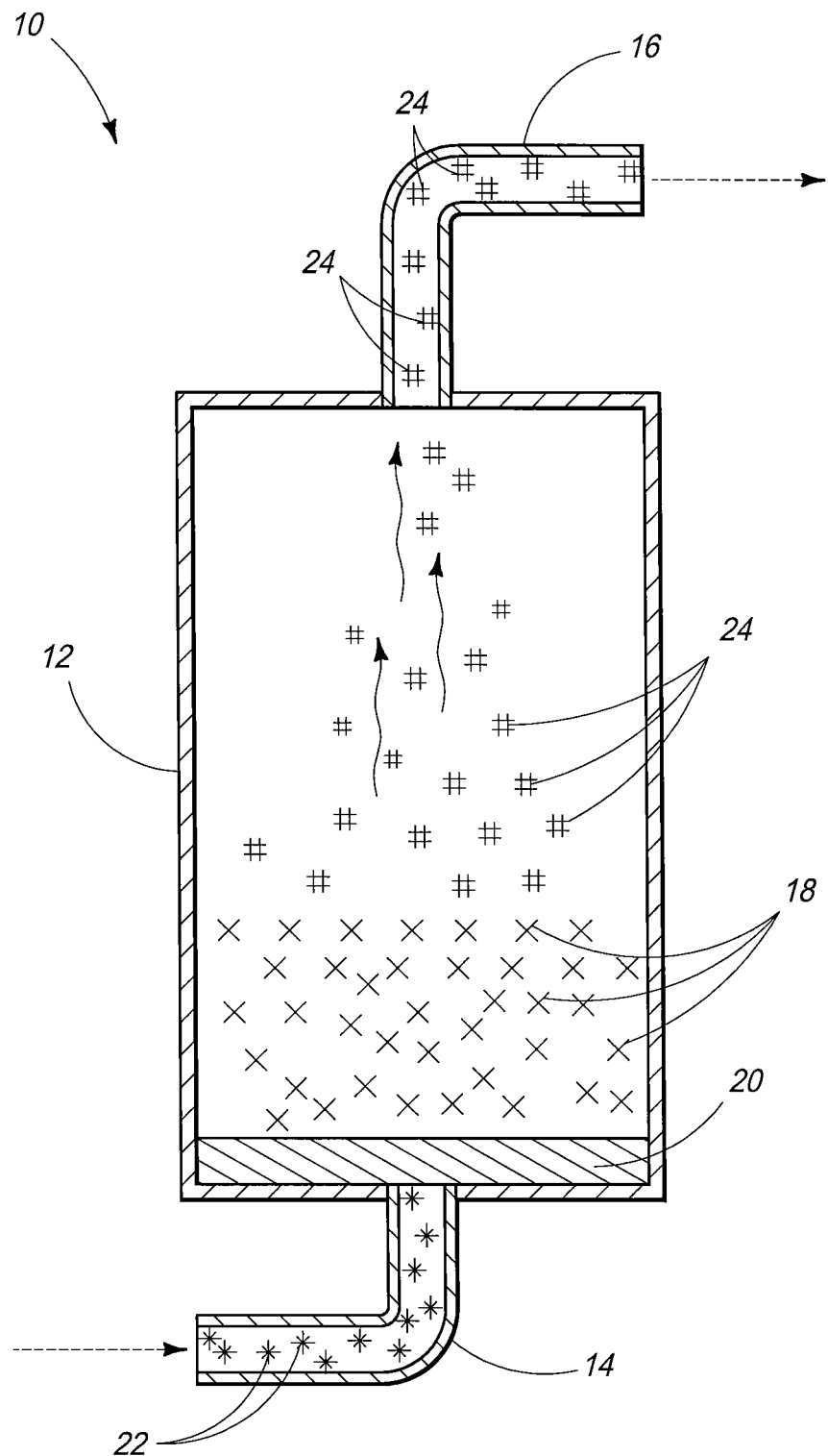
FIG. 1 is a chemical production system according to an embodiment of the disclosure.

Examples of the glycerol dehydration systems, catalysts, and methods of the present disclosure will be described with reference to FIGS. 1-10. Referring first to FIG. 1, a system 10 is shown that includes a reactor 12 having an intake 14 in fluid connection therewith and an exhaust 16 in fluid connection therewith. In accordance with example implementations, both reactor 12 and/or portions of exhaust 16 can be considered a reaction zone. Reactor 12 can be constructed of relatively inert and/or stable materials such as alloys and/or stainless steel materials, including alloys such as Inconel® for example. The reactor can be constructed as well from glass, ceramic, and/or titanium, for example. The steel components of reactor 12 may be coated as well. For example the steel components can be constructed of Silcosteel® and/or Siltek® (Restek Corporation). Intake 14 and/or exhaust 16 may be constructed of the same or different material than that of the reactor. Reactor 12 may be also configured to provide a predetermined temperature to its interior contents.

Figure 2:
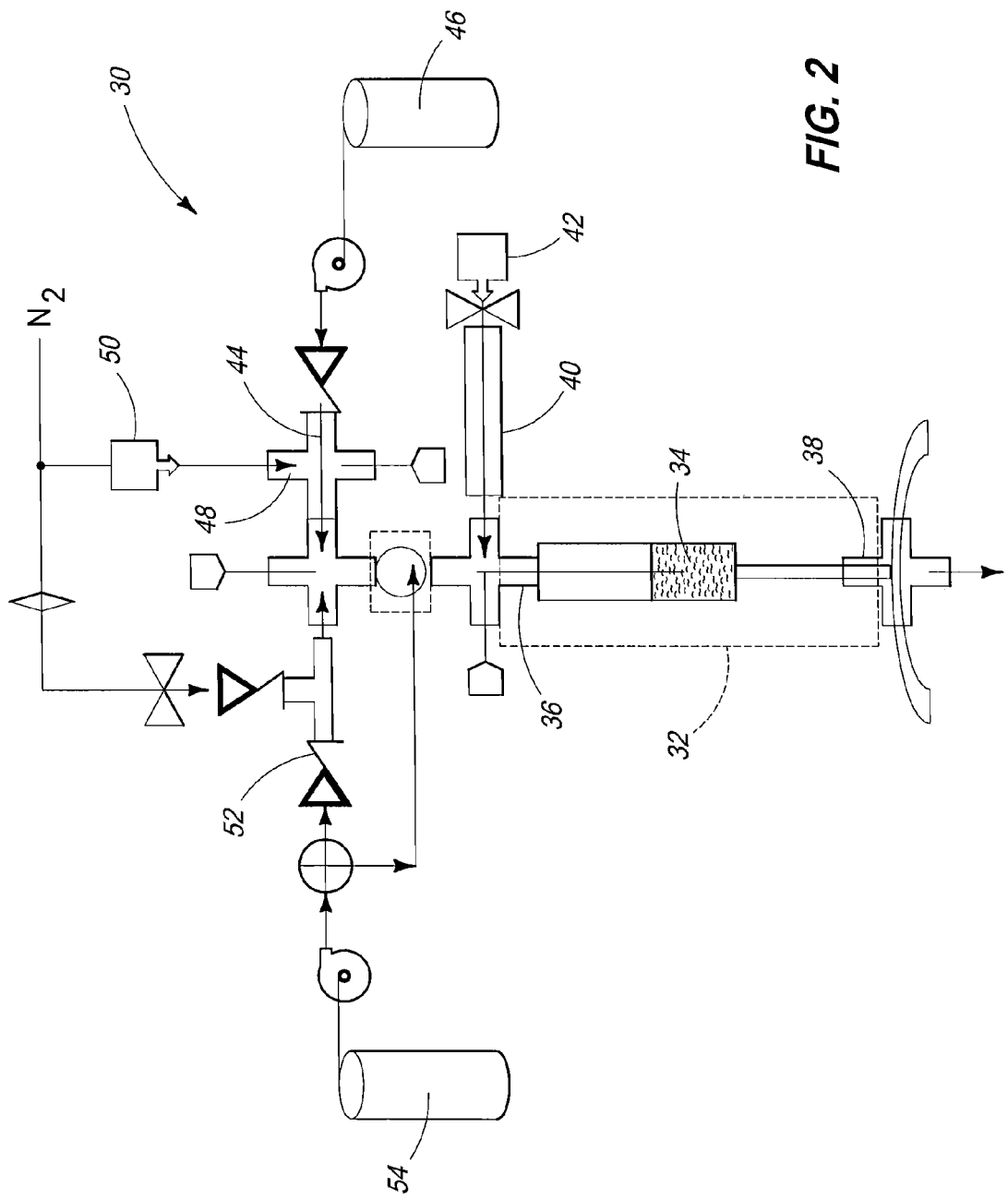
FIG. 2 is a chemical production system according to an embodiment of the disclosure.
Figure 3:
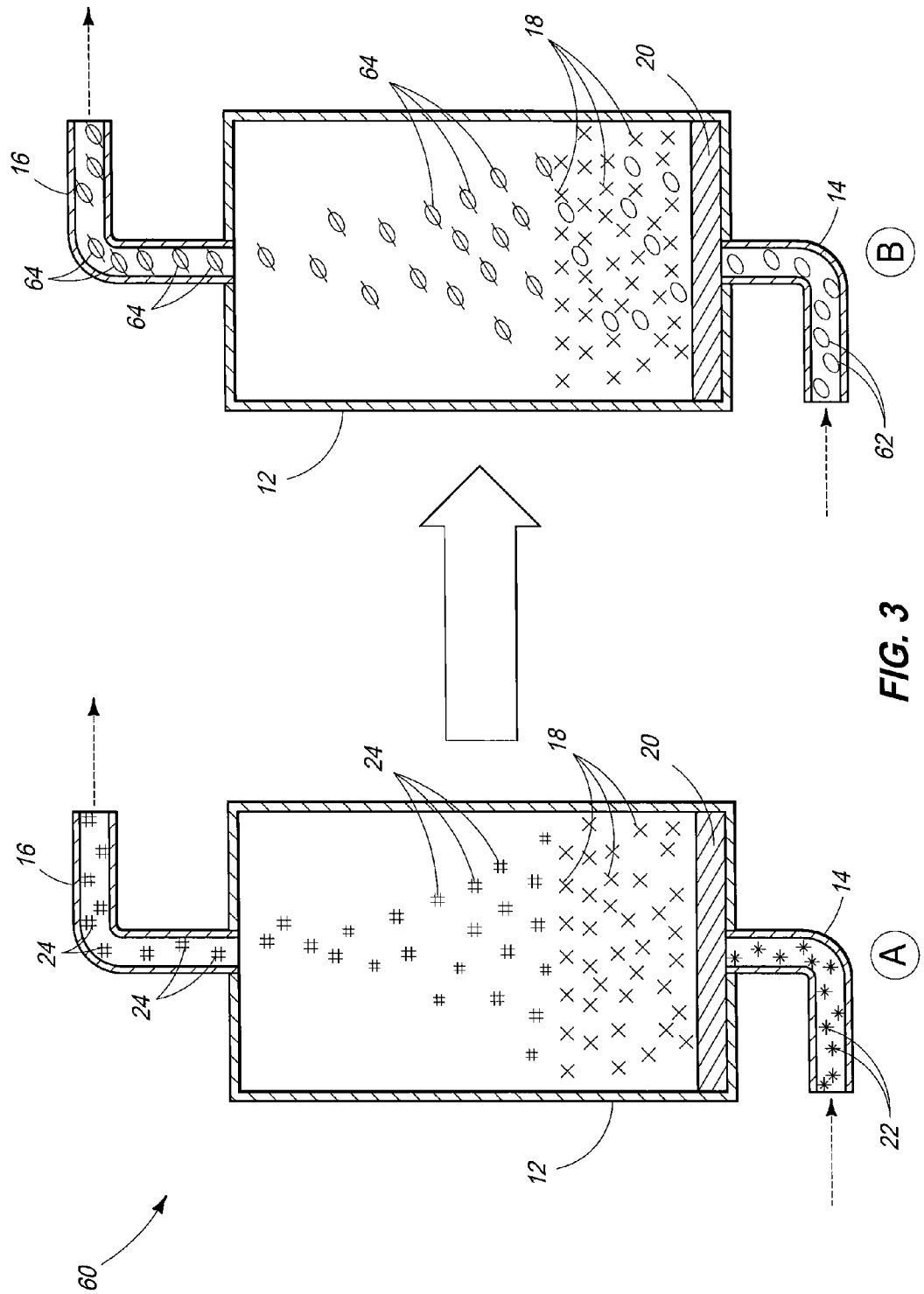
FIG. 3 is a chemical production system according to an embodiment of the disclosure.

As depicted in FIGS. 1 and 3, the flow of materials within the represented systems is from bottom to top. As depicted in FIG. 2, the flow of materials is from top to bottom. The claimed invention should not be limited to what is depicted in the drawings. Embodiments of the system may benefit from either configuration. Further, inert packing or trays 20 is represented at the bottom of the system reactor. It is to be understood that packing can exist at both the bottom and top of the reactor as well or in any desired location or locations within the reactor.

Reactor 12 can contain catalyst 18 which can be supported by packing or tray 20. Catalyst 18 within reactor 12 can include a phosphoric acid or phosphate component. According to example implementations, catalyst 18 may be referred to as a phosphorus-comprising catalyst. The phosphate component of catalyst 18 may include a phosphoric acid, monohydrogen phosphate, dihydrogen phosphate, diphosphates, polyphosphates, and/or metaphosphates. In certain embodiments, the phosphate component of catalyst 18 is a dihydrogen phosphate.

Catalyst 18 may also include at least one or more metals from groups 2-12 of the periodic table and/or Rb, K, and Cs. According to example implementations, catalyst 18 may include cobalt, Fe, K, Cs, or Rb, for example. The metals may be provided with differing states of oxidation. For example, Co may be provided as Co(II) and/or Co(III). The cobalt of the catalyst may be provided as cobalt(II)nitrate hexahydrate and/or cobalt carbonate. The ratio of metal to the dihydrogen phosphate may be about 1:2. The support material may be a fumed support material and may comprise one or more of Si, Al, Ti, and/or Zr, for example. Other stable support forms may also be used, such as gamma-alumina, structured silicas (SBA-16), or mixtures thereof.

According to an example implementation, catalyst 18 may be prepared by providing a fumed support material, then preparing a mixture comprising the support material, a phosphate material (e.g., phosphoric acid, $P_2O_5$, and/or dibasic phosphate) and at least one or more metals from groups 2-12 of the periodic table and/or Rb, K, and Cs. Prior to preparing the mixture comprising the support material, the phosphate material and at least one or more of metals from groups 2-12 of the periodic table and/or Rb, K, and Cs, the support material can be exposed to an acidic solution or calcined. This acidic solution can include nitric acid, for example, and according to another implementation, the acidic solution can comprise at least 5% v/v nitric acid and the exposing can include refluxing the support material with the solution. Calcining of the support can include heating the support material to at least 800° C. According to an example implementation, the prepared support, phosphate, and metal mixture can be dried or calcined to at least 60° C. to 800° C.

In accordance with particular implementations, a mixture of phosphoric acid and metal can be prepared. For example, an aqueous solution of phosphoric acid, such as an 85% (wt./wt.) solution (Aldrich) can be mixed with Co(II)nitrate (Aldrich) at a molar ratio of about 2 moles phosphoric acid to about 1 mole Co(II)nitrate, then diluted with water to form the mixture. To this mixture can be added silica, such as fumed silica (for example, Cabot HS-5 synthetic, amorphous, colloidal high surface area fumed silica) until gelling or slurry suspension is reached to form another mixture. (the "slurry" method) This other mixture can be dried under vacuum at about 60° C. to about 80° C., for example rotovap drying, to render a solid mixture. The solid mixture can be calcined and then sized by reducing preformed or prepared pellets using 30-70 mesh sieves. More detailed examples of catalyst preparations are disclosed below using a bulk solution that includes $Co(H_2PO_4)_2$, prepared by adding 59.62 g of $Co(NO_3)_2 \times 6H_2O$, 47.35 g of $H_3PO_4$, and 193.74 g of water.

One catalyst preparation can be prepared in a 500 mL round-bottom flask by placing 100.23 g of the above bulk solution and 83.3302 g of silica sol (Nalco 1034) drop-wise to the solution while stirring. While adding the silica sol, the solution can change from clear pink to a milky fuchsia in appearance. After addition of the silica sol, the pH can be increased to a pH of 9 to facilitate gelling (slurry). Where gelling does not occur at pH 9, the water can be roto-evaporated off to get the solution to gel and then water removed to dryness. The catalyst can then be dried during the calcination procedure, calcined, and size reduced as desired.

Another catalyst preparation can be prepared in a 500 mL Round-bottom flask by placing 100.24 g of the above bulk solution and 70.8379 g of silica sol (Ludox AS-40) dropwise to the solution while stirring. While adding the silica sol, the solution can change from clear pink to a milky purple. After addition of the silica sol the solution can be heated to facilitate gelling (slurry). Where no gelling occurs the water can be roto-evaporated off to get the solution to gel and then the water removed to dryness. The catalyst can then be dried during the calcination procedure, calcined, and size reduced.

Yet another catalyst preparation can be prepared in a 500 mL round-bottom flask by placing 100.23 g of the above bulk solution and 28.3 g of HS-5 silica (Cabot). While adding the HS-5, the solution may gel and water may be added to get a uniform solution (slurry). The solution can be stirred overnight and the water roto-evaporated off to dryness. The catalyst can then be dried during the calcination procedure, calcined, and size reduced.

Catalyst can also be prepared in a 400 mL jar by placing 14.9 g of HS-5 silica (Cabot HS-5) and drop-wise adding a solution comprised of 6.5 g of $Co(NO_3)_2$—$6H_2O$, 5.06 g of $H_3PO_4$ and 26.3 g of $H_2O$. The above bulk solution is added drop-wise while mixing until incipient wetness is achieved. (the "incinpient wetness impregnation" method aka "IWI") The solution can then be dried overnight in an oven to dryness. The catalyst can then be dried during the calcination procedure, calcined, and size selected as desired.

In accordance with another embodiment, a Rb-catalyst can be prepared and utilized to dehydrate a multihydric compound such as glycerol. As example, $RbH_2PO_4$ catalyst can be prepared using $RbCO_3$ and $H_3PO_4$ in combination with an HS-5 Fumed Silica Slurry as described above. Water can be removed from the preparation via rotary evaporation, the remaining solids can be dried and then calcined at 600° C. for 4 hours. In accordance with more specific implementations, a solution of Silica (HS-5 Fumed Silica), Rubidium carbonate ($Rb_2CO_3$), and Phosphoric Acid ($H_3PO_4$) can be prepared by adding 9.99 g, 3.22 g, and 4.63 g of each (respectively) to 100 g Water in a 500 mL Jar and stirred overnight. An amount of $CO_2$ may then evolve from the solution. The solution can then be placed on the rotary evaporator and the water removed. The remaining solids can then be placed in a drying oven overnight prior to calcination.

The calcination procedure referenced above can include heating the roto-evaporated mixture to 100° C. at 0.5° C./min and maintaining the mixture at that temperature for 2 hrs, after which the temperature of the mixture can be ramped to 600° C. at 2° C./min and held for 4 hrs, then cooled to room temperature prior to or after size reduction to yield a prepared catalyst.

Referring to FIG. 1, packing 20 such as quartz and/or steel wool can be provided to reactor 12. The packing can facilitate the support of the catalyst within reactor 12 as well as a more uniform distribution of both intake materials and exhaust materials. As such packing 20 can be provided both above and below catalyst 18 which can be loaded into reactor 12. Both catalyst 18 and packing 20 can consume substantially all of the volume defined by reactor 12, thereby leaving very little void volume. Further, the catalyst may be diluted with a relatively inert material such as quartz or alpha alumina if desired. In accordance with example implementations dilution of the catalyst with a relatively inert material can improve heat and mass transfer throughout the catalyst bed.

Intake 14 can be coupled to a reactant reservoir or reactant mixture reservoir, not shown. Intake 14 can also be described as a conduit coupling reactor 12 to a reactant reservoir. System 10 can be configured to expose reactant from the reactant reservoir to catalyst 18 to form product 24 from reactant 22. Prior to exposing reactant 22 to catalyst 18, catalyst 18 can be readied for catalysis. Readying catalyst 18 for catalysis can include providing nitrogen and/or air to catalyst 18 via intake 14 while maintaining a temperature of the catalyst within the reactor between 250° C. and 350° C. After exposing the catalyst to the nitrogen and/or air, the catalyst can be exposed to water and nitrogen and/or air via intake 14 while maintaining the temperature of the catalyst within the reactor between 250° C. and 350° C. Water can be about 95% of the mixture being exposed to the catalyst during this readying phase while the nitrogen and/or air can be 5%. After readying catalyst 18, reactant 22 can be exposed to catalyst 18 via intake 14.

Reactant 22 can be in the form of a mixture and/or a pure reactant stream. As a mixture, Reactant 22 can include more than one multihydric compounds, a single multihydric compound, and/or diluents such as water and/or gases such as nitrogen. Reactant 22 can include a crude biofuel product. Reactant 22 can comprise a multihydric compound such as glycerol, for example. The glycerol can be a co-product of biofuel production. According to example implementations, the glycerol of reactant 22 may be in the form of a purified glycerol and/or a crude glycerol co-product. The reactant 22 can contain glycerol in an amount between 3% and 70% (wt/wt); between about 8% and 10% (wt./wt.); between about 25% and 30% (wt./wt.); and in specific embodiments, the reactant 22 can comprise at least about 25% (wt/wt) glycerol and/or less than 70% (wt/wt).

Reactant 22 can also include carrier materials as well. According to example implementations, reactant 22 can include glycerol, water, $N_2$, and/or $CO_2$. The reactant can include water in an amount as high as 97% (wt./wt.). In accordance with example implementations, the reactant 22 can include glycerol in an amount between 3% and 70% (wt./wt.), water in an amount as high as 97% (wt./wt.), and $CO_2$ and/or $N_2$ in amounts (either alone or by combined weights) between 1% and 5% (wt./wt.).

According to example implementations, reactant 22 can have a temperature of at least about 110° C. prior to being exposed to catalyst 18. In accordance with other implementations, reactant 22 can be heated to about the same temperature as that of the catalyst in the reactor. As another example, reactant 22 can be heated to about 300° C. prior to entering reactor 12.

Reactant 22 can be exposed to the reaction zone and catalyst 18 via intake 14 by facilitating a pressure differential across intake 14 to reactor 12. To facilitate the exhaust of products from exhaust 16, the pressure differential can be facilitated through to exhaust 16. This pressure differential can be facilitated via pumps, for example, placed up stream of intake 14 or downstream of exhaust 16. The pumps can facilitate the flow of materials through reactor 12 and this flow can be quantitated as the Weight Hourly Space Velocity (WHSV, gram multihydric reactant/gram catalyst/hour) and/or the Gas Hourly Space Velocity (GHSV, total gas volume feed/volume catalyst/hour). A residence time of the reactant can be calculated from the inverse of the GHSV.

Reactant 22 can be provided to system 10 at a WHSV ranging from about 0.02 to about 12. Reactant 22 can also be provided to system 10 at a GHSV of from about 500 to about 60,000. Reactant 22 should have a residence time exposed to catalyst 18 of from about 0.001 to about 7 seconds. In accordance with example implementations, the residence time is about 0.45 seconds. These flow parameters of system 10 can be facilitated by manipulating the pressure differential across system 10 utilizing flow pumps for example. In accordance with specific configurations, a back pressure of reactant 22 provided to reactor 12 can be less than 5 psig.

Referring to FIG. 2, a system 30 is shown. Intake 36 can be coupled to one or more conduits, for example, dry air conduit 40, water conduit 44, into conduit 48 and/or glycerol conduit 52. Consistently, these additional conduits can be coupled to reservoirs, for example, dry air conduit 40 can be coupled to dry air reservoir 42, water conduit 44 can be coupled to water reservoir 46, conduit 48 can be coupled into reservoir 50, and glycerol conduit 52 can be coupled to glycerol reservoir 54. These conduits can be coupled to intake 36 via valves, blowers, and/or pumps, for example, to facilitate control and/or flow of materials from the representative reservoirs. Intake 36 can also be couple to reactor assembly 32 that includes catalyst 34 and exhaust 38. As depicted in FIG. 2, a system 30 can be configured to facilitate the individual control of components entering reactor assembly 32. Further, these components can enter reactor assembly 32 from the top toward the bottom for exhaustion via exhaust 38.

Referring to FIG. 1, reactant 22 including glycerol may be exposed to catalyst 18 to form product 24. Product 24 can include a dehydration product of a multihydric compound. For example product 24 can include the dehydration product acrolein of the multihydric compound glycerol. One or both of acrolein and/or acetol can be the product of the dehydration of glycerol as well as byproducts.

System 10 can include exhaust 16 configured to receive product 24 from reactor 12. Exhaust 16 can be coupled to a product reservoir not shown, and/or coupled to a product purification assembly not shown. Product purification assemblies can include distillation assemblies and/or drying assemblies, for example. Exhaust 16 can be considered a conduit coupling reactor 12 to a product reservoir, not shown.

In accordance with example implementations the catalyst can be supported rather than unsupported. $Co(H_2PO_4)_2$ on Nalco Silica Sol may thus be preferred to bulk (unsupported) $Co(H_2PO_4)_2$. When referring to the catalyst in the context of the present specification, it is to be understood that the catalyst is referenced in terms of its precursor materials and the molar ratio of same. The actual chemical composition of the catalyst during reaction while determinable was not determined for every assay completed. As an example, $Co(H_2PO_4)_2$ on silica may be the chemical composition but after calcination this composition can be $Co_2P_2O_7$. Referring to Table 1 below, a comparison of supported and unsupported catalysts (referenced by precursor materials and prepared in accordance with the description above) is provided.

TABLE 1

| Catalyst | wt % PO4 | TOS (min.) | GHSV (1/hr) | WHSV ($g_{gly}/g_{cat}$/hr) | glycerol | steam | nitrogen | wt % gly Feed | Acrolein Productivity ($g_{acrolein}/g_{cat}$/hr) | Conversion (%) | Acrolein Selectivity (%) |
|---|---|---|---|---|---|---|---|---|---|---|---|
| | | | | | (Partial Pressure (atm)) | | | | | | |
| $Co(H_2PO_4)_2$ unsupported | 75.1 | 20 | 77,018 | 15.14 | 0.052 | 0.872 | 0.076 | 23.3 | 0.011 | 0.4 | 30.6 |
| | | 100 | 77,018 | 15.14 | 0.052 | 0.872 | 0.076 | 23.3 | 0.004 | 0.1 | 39.8 |
| $Co(H_2PO_4)_2$ on Nalco Silica Sol | 26 | 20 | 70,275 | 22.95 | 0.08 | 0.845 | 0.075 | 33.1 | 0.624 | 5.3 | 84.3 |
| | | 110 | 70,275 | 22.95 | 0.08 | 0.845 | 0.075 | 33.1 | 0.478 | 4.2 | 81.4 |
| $Co(H_2PO_4)_2$ on Nalco Silica Sol | 26 | 10 | 74,172 | 24.16 | 0.086 | 0.888 | 0.026 | 33.1 | 0.949 | 7.7 | 83.8 |
| | | 20 | 74,172 | 24.16 | 0.086 | 0.888 | 0.026 | 33.1 | 0.846 | 6.9 | 83.4 |
| | | 30 | 38,032 | 12.08 | 0.084 | 0.865 | 0.051 | 33.1 | 0.747 | 12.5 | 81.3 |
| | | 60 | 38,032 | 12.08 | 0.084 | 0.865 | 0.051 | 33.1 | 0.742 | 12.4 | 81.4 |
| | | 90 | 38,032 | 12.08 | 0.084 | 0.865 | 0.051 | 33.1 | 0.674 | 11.3 | 81.1 |

In accordance with an example implementation, a $Co(H_2PO_4)_2$ on Nalco Silica Sol with a reaction zone can be used to facilitate the dehydration of glycerol to acrolein in accordance with the parameters in Table 2 below.

TABLE 2

| Catalyst | wt % PO4 | TOS (min.) | GHSV (1/hr) | WHSV ($g_{gly}/g_{cat}$/hr) | glycerol | steam | nitrogen | wt % gly Feed | Acrolein Productivity ($g_{acrolein}/g_{cat}$/hr) | Conversion (%) | Acrolein Selectivity (%) |
|---|---|---|---|---|---|---|---|---|---|---|---|
| | | | | | Partial Pressure (atm) | | | | | | |
| $Co(H_2PO_4)_2$ on Nalco Silica Sol | 26 | 10 | 8,389 | 1.34 | 0.042 | 0.748 | 0.21 | 22.4 | 0.731 | 100 | 89.6 |
| | | 60 | 8,389 | 1.34 | 0.042 | 0.748 | 0.21 | 22.4 | 0.719 | 100 | 88.1 |
| | | 140 | 8,389 | 1.34 | 0.042 | 0.748 | 0.21 | 22.4 | 0.728 | 100 | 89.3 |

According to example implementations, a byproduct within product 24 can be a carbon-based byproduct, such as coke. The carbon byproduct can include conjugated carbon compounds having an average combustion temperature (in pure oxygen) of from between 250° C. and 800° C. It has been recognized that these byproducts can inhibit the continuous use of system 10 to produce product 24 from reactant 22. As an example, it has been recognized that carbon based byproducts can inhibit the ability of catalysts to facilitate the conversion from reactant 22 to product 24 as well as impede the progress of reactants and/or products through the entirety of system 10, for example by clogging system 10.

Referring to FIG. 4 for example, plotted data is shown that can be acquired utilizing the systems, methods and catalysts of the present disclosure. According to example implementations, the GHSV can be about 7,600 per hour. As the example dictates, the partial pressure of glycerol can be about 0.084 while the partial pressure of water can be about 0.891 and the partial pressure of nitrogen can be 0.026. The process can be performed at a total pressure of 1 atmosphere with a temperature of about 280° C. In accordance with this data, as the pressure differential on the system rises from about 1.5 psig to 22 psig the conversion of the system deceases, demonstrating that plugging is occurring in the system.

It has been recognized that during the process different types of carbon byproducts can be generated. Carbon byproduct can take the form of soft or hard carbon byproducts, with the soft carbon byproducts being those carbon byproducts that may be removed from the system at temperatures from about 250° C. to about 400° C., and the hard carbon byproducts being removed from the system at temperatures from about 400° C. to about 800° C. Referring to FIG. 4A, portions of spent catalyst bed were sampled and it was recognized that the upper portion (i.e, closest to feed inlet) contained primarily soft carbon byproduct while the lower portion (i.e., closest to product exit) contained primarily hard carbon byproduct.

Referring next to FIG. 4B, three glycerol dehydration processes were performed and the reactor components were sampled for carbon byproduct. As shown the reactor segments where plugging occurred contained a majority of hard carbon byproduct with a combustion temperature as high as 780° C. It has been recognized that the carbon byproducts formed inside the reaction zone, but outside the catalyst bed may be the primary cause for pressure build up, as product retention within the reactor prevented product removal and in turn caused formation of carbon on the catalyst.

It has been recognized that the formation of the soft carbon byproduct is more desirable than the hard carbon byproduct for at least the reason that it may be removed at lower temperatures. Temperatures as low as the reaction temperatures of the disclosed process, from about 250° C. to about 350° C., may be used to remove soft carbon byproduct from the system. In accordance with example embodiments, soft carbon byproduct generated during the production process can be removed with or without regeneration of the system.

According to example implementations, systems and methods of the present disclosure include parameters that can limit carbon byproduct formation to an acceptable amount and/or type of carbon byproduct, thus providing for the formation of sufficient product 24 with the sufficiency being in terms of production rate, and production rate can include one or both of reactant selectivity and/or reactant conversion.

In one implementation, glycerol can be exposed to a phosphorous-comprising catalyst to form acrolein. As an example, dehydration product production rate can include the acrolein productivity where the reactant is glycerol. This can be the weight of acrolein produced per unit weight of catalyst per unit time (e.g., g-acrolein/g-catalyst/hr). The conversion of the glycerol can be reported as a percentage of glycerol reacted. The selectivity of the process to form acrolein rather than some other product can likewise be reported as a percentage.

At the outset of the process, initial rates can be recorded. For example, initial product rates, initial conversion and/or initial selectivity rates can be recorded. Further, the back pressure provided to intake 14 can also be recorded at the outset of the process as an initial back pressure. When utilizing the system during the dehydration process, when one or a combination of all these parameters decrease by a substantial amount, the formation of product 24 can no longer be considered sufficient. For example, where selectivity and/or conversion decreases by 10-15%, and/or the back pressure increases by a factor of 4-5, for example, to 4-5 psig from 1 psig, to 20 or 25 psig from 4-5 psig, and/or a factor of 10 such as to 50 psig from 5 psig, excessive carbon byproduct has accumulated on the catalyst or within the reactor. These parameters can be an indication of system strain such as a system clogged from production of carbon byproducts. FIG. 4 is demonstrative of a system that is strained.

Where it is the case that product generation is no longer sufficient, it has been determined that systems of the present disclosure can be regenerated, in part by regenerating the system itself and/or the catalyst within the system. According to example implementations, regeneration of the system can include removing byproducts from the system, including carbon based byproducts.

Referring to FIG. 3, system 60 is shown that depicts the same system in configurations A and B. System 60 can be a system that is configured to cyclically produce dehydration product and regenerate the reaction zone. Configuration A can be consistent with that of system 10 described herein, or a system configured to produce the dehydration product of a multihydric compound from within a reaction zone. Configuration B is that of system 10 after being utilized to perform dehydration and thereby containing a used glycerol dehydration catalyst. As an example, in configuration A the production of the dehydration product can include exposing reactant from a reactant reservoir to the catalyst within the reaction zone to form the dehydration product at a production rate. In configuration B, the regenerating the reaction zone can include returning the reaction zone to produce the dehydration product at a rate of at least 70%, more preferably at least 80%, and most preferably at least 90% of the production rate at the beginning of a cycle.

In accordance with example implementations processes can include after ceasing the providing of the reactant, a phosphorous-comprising material can be provided to the reactor. The phosphorous-comprising material can increasing the amount of phosphorous in the dehydration catalyst. In some configurations, the amount and/or type of phosphorous of the catalyst may be depleted during the exposing of the catalyst to the multihydric compound and/or during regeneration. Without removing the catalyst from the reaction zone, the catalyst can be supplemented or rephosphated, for example. After providing the phosphorous-comprising material, reactant can again be exposed to the catalyst. This rephosphating can be integrated into a cyclic production method that includes one or more of exposing, regenerating, and rephosphating as desired by the operator of the production facility. The phosphorous-comprising material utilized to rephosphate can include an organophosphate such as tributylphosphate and/or trimethyl phosphate, for example. This material can be exposed to the catalyst and then the catalyst dried under air followed by exposing the catalyst to water prior to exposing the catalyst once again to reactant, for example.

By maintaining a catalyst that can be regenerated to this extent and avoiding losses in yield that may only be remedied through removal and refurbishment or replacement of catalyst, preferably the system retains an economically sustainable level of productivity compared to its demonstrated initial peak productivity under normal operating conditions, after at least 1000 hours, more preferably at least 2000 hours and still more preferably at least 4000 hours online for a given catalyst charge under process conditions.

Production and regeneration can be performed in accordance with multiple parameters. While shown in FIG. 3 as single conduits entering reactor 12, it is understood that the single conduit can either represent multiple conduits directly entering reactor 12 and/or a single conduit receiving multiple conduits via unions prior to intake 14, for example. As an example, glycerol can be provided to the reactor via one conduit and water can be provided to the reactor via another conduit. The catalyst can be exposed to the glycerol to form a dehydration product and the exposing the catalyst to the glycerol ceased, and after ceasing exposing the catalyst to the glycerol, the catalyst can be exposed to water with the water being primarily in the gaseous form. After a time, then glycerol can again be provided to the reactor to form a dehydration product.

Referring to an alternative method for performing the process, carbon byproducts can be formed while preparing product 24 via exposing a multihydric reactant to the dehydration catalyst. The exposing of the multihydric reactant to the dehydration catalyst can be stopped and then after stopping the exposing, the system itself as well as the catalyst can be exposed to a flowing gas and the contents of the system heated to a temperature sufficient to release at least a portion of the carbon byproducts from the reactor. After heating the contents of the reactor, a multihydric reactant can again be provided to the reactor to form product 24.

Processes of the present disclosure can include ceasing the providing of reactant 22 to reactor 12, and after ceasing the providing of the reactant, providing a gas 62 to the reactor while maintaining the temperature of the catalyst of the reactor below 800° C. The gas can be a component of the regeneration mixture, for example. Such regeneration mixture can include water alone, dry air, $N_2$, and/or $CO_2$ alone, for example, or in combination. According to an example implementation, the regeneration mixture can include an oxidizing reagent, for example, and this regeneration mixture can be provided to the reactor after ceasing providing of the multihydric reactant such as glycerol. While providing this oxidizing reagent, the temperature of the catalyst can be maintained below 800° C. and then after providing the reagent, again providing glycerol to the reactor. Upon providing gas 62 byproducts 64 may be removed from system 60 via exhaust 16.

According to example implementations as described above, the reactant 22 can include a multihydric reactant such as glycerol, as well as water. The transition to regeneration can include ceasing the providing of the multihydric reactant while maintaining the providing of the water to the reactor. The water being provided to the reactor can be in the gaseous form, for example, and then upon providing sufficient gaseous water, the reactant mixture can be provided again to the reactor.

As an example, where reactants 22 include a multihydric reactant such as glycerol, water and $N_2$, the multihydric reactant can be stopped, and the water and $N_2$ allowed to proceed to and through reactor 12 as a part of configuration B. In accordance with example implementations this can be considered a flushing of reactants from the system. This flushing of reactants can continue for a predetermined period of time and/or exhaust 16 monitored for reactants, products, and/or byproducts. During the monitoring, the system may be considered to be fully flushed when the amount(s) of reactants, products, and/or byproducts in exhaust 16 stabilize over time, for example, varying by less than 5%/min. While monitoring to verify the system has been fully flushed, the back pressure may be monitored as well.

After regeneration is completed, it may be desirable to return the system to a production or on-line mode, where reactant is provided to the system. For example, where it is the case that back pressure had risen substantially and returned to the initial back pressure during flushing, it may be desirable to continue to provide reactant to the system. Where there is no change in back pressure it can be desirable to continue regeneration.

Regeneration of the system may also be continued by decreasing the amount of water being provided to the system and/or increasing the amount of $N_2$. After decreasing and/or ceasing the amount of water to the system, air may be provided to the system. In accordance with example implementations, from 5-500 sccm of $N_2$ and/or from about 5-1,000 sccm of air can be provided to the system. While providing the $N_2$ and/or air to the system, the system can be heated from reaction temperature (or lower) to a temperature between 550° C. and 800° C. The heating of the system can be done according to a temperature ramp. For example, the ramp can be from 1° C./min to about 40° C./min; from 1° C./min to about 10° C./min; from 1° C./min to about 5° C./min; from 5° C./min to about 10° C./min; and/or from 10° C./min to about 40° C./min. During the heating in the regeneration process, large amounts of byproducts and/or their decomposition products may be removed from the system. It has been recognized that it can be desirable to remove these byproducts slowly rather than quickly in order to avoid plugging the system with byproducts evolving from exhaust 16, or avoidance of excessive thermal gradients developing during their removal.

In accordance with example implementations, heating can be performed in cycles based on the amount of $N_2$ and/or air provided through the system. In accordance with this and other implementations, the amount of byproduct and/or byproduct residue, such as $CO_2$, can be monitored and when the decrease in the amount monitored stabilizes over time the heating process can be halted. As an example, when the change in the amount of $CO_2$ is less than 5%/min, the system can be considered regenerated. As another example, the amount of $CO_2$ can be compared to a threshold amount, such as an amount recorded during the process and/or after a previous regeneration, and when this amount is substantially the same as the amount monitored during heating, the system can be considered regenerated.

It has been recognized that simply heating the system to temperatures higher than 800° C., while expedient for removal of byproducts, can degrade the catalyst to practical inertness. For example, it has been recognized that the activity of the catalyst can be degraded via the formation of crystalline pyrophosphates from the catalyst itself. The presence of crystalline pyrophosphates of the form $M_2P_2O_7$ (where M is a metal or metals from groups 2-12, such as cobalt) has been associated with a catalyst that has undergone performance degradation in terms of selectivity and/or conversion of the multihydric compound. This further stresses the importance of running the system under parameters that tend not to produce the hard carbon byproduct disclosed above. For example, the regeneration of 26 wt % $PO_4$ as $Co(H_2PO_4)_2$ on Nalco Silica Sol and $Co(H_2PO_4)_2$ on HS-5 Fumed Silica were performed. The regeneration was performed in accordance with the following parameters:

1. Initial heating in nitrogen from room temperature to 280° C.
2. Introduction of steam for 30 minutes
3. Introduce glycerol/steam/nitrogen for 30 minutes
4. Terminate glycerol flow, steam/nitrogen flow for 5-10 minutes
5. Stop steam flow, nitrogen flow only for 5 minutes
6. Start air flow and temperature ramp to 540° C. in 20 minutes
7. Hold 45-60 minutes
8. Cool to 280° C.
9. Start steam for 30 minutes
10. Start glycerol feed (cycle 2)
11. Repeat steps 4-9
12. Start glycerol feed (cycle 3)

Referring to Table 3 below, the production rates of the non-fumed silica supported catalyst are shown utilizing the regeneration parameters specified above along with the production parameters specified in the Table.

TABLE 3

| Catalyst | Cycle | TOS (min.) | GHSV (1/hr) | WHSV ($g_{gly}/g_{cat}/hr$) | glycerol | steam | nitrogen | wt % gly Feed | Acrolein Productivity ($g_{acrolein}/g_{cat}/hr$) | Conversion (%) | Acrolein Selectivity (%) |
|---|---|---|---|---|---|---|---|---|---|---|---|
| | | | | | Partial Pressure (atm) | | | | | | |
| $Co(H_2PO_4)_2$ | 1 | 0-10 | 35,670 | 7.65 | 0.084 | 0.891 | 0.026 | 32.5 | 0.325 | 8.4 | 82.8 |
| on Nalco | | 10-20 | 35,670 | 7.65 | 0.084 | 0.891 | 0.026 | 32.5 | 0.601 | 15.5 | 83.4 |
| Silica Sol(26 | | 20-30 | 35,670 | 7.65 | 0.084 | 0.891 | 0.026 | 32.5 | 0.688 | 17.3 | 85.2 |
| wt % PO4) | 2 | 0-10 | 35,670 | 7.65 | 0.084 | 0.891 | 0.026 | 32.5 | 0.019 | 2.7 | 15.0 |
| | | 10-20 | 35,670 | 7.65 | 0.084 | 0.891 | 0.026 | 32.5 | 0.466 | 12.5 | 80.0 |
| | | 20-30 | 35,670 | 7.65 | 0.084 | 0.891 | 0.026 | 32.5 | 0.479 | 12.4 | 83.0 |
| | 3 | 0-10 | 35,670 | 7.65 | 0.084 | 0.891 | 0.026 | 32.5 | 0.008 | 2.4 | 7.7 |
| | | 10-20 | 35,670 | 7.65 | 0.084 | 0.891 | 0.026 | 32.5 | 0.272 | 8.1 | 72.2 |
| | | 20-30 | 35,670 | 7.65 | 0.084 | 0.891 | 0.026 | 32.5 | 0.319 | 8.5 | 80.8 |

Referring to Table 4 below, the production rates of the fumed silica supported catalyst are shown for comparison, utilizing the regeneration parameters specified above along with the production parameters specified in the Table.

TABLE 4

| Catalyst | Cycle | TOS (min.) | GHSV (1/hr) | WHSV ($g_{gly}/g_{cat}$/hr) | glycerol | steam | nitrogen | wt % gly Feed | Acrolein Productivity ($g_{acrolein}/g_{cat}$/hr) | Conversion (%) | Acrolein Selectivity (%) |
|---|---|---|---|---|---|---|---|---|---|---|---|
| | | | | | \multicolumn{3}{c|}{Partial Pressure (atm)} | | | | |
| $Co(H_2PO_4)_2$ on | 1 | 0-9 | 36,858 | 12.01 | 0.086 | 0.888 | 0.026 | 33.1 | 1.188 | 19.1 | 85.1 |
| Cabot HS-5 | | 9-14 | 36,858 | 12.01 | 0.086 | 0.888 | 0.026 | 33.1 | 1.386 | 22.2 | 85.3 |
| Fumed Silica | | 14-19 | 36,858 | 12.01 | 0.086 | 0.888 | 0.026 | 33.1 | 1.373 | 21.8 | 86.1 |
| (26 wt % PO4) | | 19-24 | 36,858 | 12.01 | 0.086 | 0.888 | 0.026 | 33.1 | 1.305 | 20.8 | 85.7 |
| | | 24-29 | 36,858 | 12.01 | 0.086 | 0.888 | 0.026 | 33.1 | 1.288 | 20.5 | 86.0 |
| | | 29-34 | 36,858 | 12.01 | 0.086 | 0.888 | 0.026 | 33.1 | 1.427 | 22.1 | 88.4 |
| | 2 | 0-5 | 36,858 | 12.01 | 0.086 | 0.888 | 0.026 | 33.1 | 1.096 | 17.3 | 86.4 |
| | | 5-10 | 36,858 | 12.01 | 0.086 | 0.888 | 0.026 | 33.1 | 1.449 | 23.1 | 85.6 |
| | | 10-15 | 36,858 | 12.01 | 0.086 | 0.888 | 0.026 | 33.1 | 1.455 | 23.3 | 85.4 |
| | | 15-20 | 36,858 | 12.01 | 0.086 | 0.888 | 0.026 | 33.1 | 1.523 | 24.3 | 85.8 |
| | | 20-25 | 36,858 | 12.01 | 0.086 | 0.888 | 0.026 | 33.1 | 1.513 | 24.2 | 85.5 |
| | | 25-30 | 36,858 | 12.01 | 0.086 | 0.888 | 0.026 | 33.1 | 1.268 | 20.3 | 85.4 |
| | | 30-35 | 36,858 | 12.01 | 0.086 | 0.888 | 0.026 | 33.1 | 1.747 | 28.4 | 84.2 |
| | 3 | 0-10 | 36,858 | 12.01 | 0.086 | 0.888 | 0.026 | 33.1 | 1.206 | 20.4 | 80.9 |
| | | 10-20 | 36,858 | 12.01 | 0.086 | 0.888 | 0.026 | 33.1 | 1.349 | 22.9 | 80.5 |
| | | 20-30 | 36,858 | 12.01 | 0.086 | 0.888 | 0.026 | 33.1 | 1.431 | 23.0 | 85.3 |
| | | 20-38 | 36,858 | 12.01 | 0.086 | 0.888 | 0.026 | 33.1 | 1.431 | 23.0 | 85.3 |

As can be seen, the fumed support demonstrates substantial improvement over the non-fumed support.

Where process parameters are utilized that produce the hard carbon byproduct, regeneration temperatures below 400° C. will generally be ineffective to remove the hard carbon byproduct. Where regeneration temperatures are increased above 400° C. to remove the hard carbon byproduct, pyrophosphates of the form $M_2P_2O_7$ can be produced from the catalyst rendering the catalyst inactive by this means.

Embodiments of both the dehydration methods described herein as well as the regeneration methods of the present disclosure provide production facilities that can maintain an effective and active catalyst. Included are catalyst formulations and catalyst preparation methods to provide materials which do not form excessive amounts of pyrophosphate even at the temperatures required for hard carbon by product removal, such as 550° C.

After regeneration, the system can be cooled to from about 250° C. to about 350° C., then, prior to exposing reactant 22 to catalyst 18, catalyst 18 can be readied for catalysis. Readying catalyst 18 for catalysis can include providing $N_2$ and/or air to catalyst 18 via intake 14 while maintaining a temperature of the catalyst within the reactor between 250° C. and 350° C. After exposing the catalyst to the $N_2$ and/or air, the catalyst can be exposed to water and $N_2$ and/or air via intake 14 while maintaining the temperature of the catalyst within the reactor between 250° C. and 350° C. Water can be about 95% of the mixture being exposed to the catalyst during this readying phase while the $N_2$ and/or air can be 5%. After readying catalyst 18, reactant 22 can be exposed to catalyst 18 via intake 14. This readying can facilitate configuration A of FIG. 3.

Systems 10, 30, and/or 60 can be part of an overall production facility for conducting chemically synthetic dehydration processes. As shown in FIG. 1 for example, system 10 includes a single reactor 12, but it is contemplated that system 10 can be part of a larger system that includes multiple reactors configured, for example, to perform continuous dehydration processes. For example, a reactor may be "on line" while another reactor may be "off line." According to this example embodiment, reactors on line may be utilized to perform dehydration while reactors off line may be utilized to regenerate catalysts or prepare new catalysts to perform the dehydration process.

Referring to FIG. 5, a plot is shown demonstrating the regeneration of a system wherein the reactant mixture is provided to a system at a GHSV of 21,664 converting 2.43 grams glycerol per gram catalyst per hour with the reactant mixture having a weight % of glycerol at 18.8%. Glycerol is ceased being provided to the system and water and/or air is provided to regenerate the system. Further removal of carbon plugs downstream of the catalyst bed was performed. Glycerol is returned to the system at a GSHV of 21,184 to convert 2.43 grams glycerol per gram catalyst per hour.

Referring to FIGS. 6 and 7, two additional glycerol dehydration/reaction and regeneration cycles are shown in the same system. Accordingly, in the first cycle referenced as "J11" and "J11 regeneration", the WHSV was at 12 grams glycerol per gram catalyst per hour, and the GHSV at 37,000 per hour. The partial pressure of glycerol was 0.086 and the partial pressure of water was 0.888, with a partial pressure of nitrogen being 0.026. The catalyst was regenerated under air at 545° C. for hour. For the second cycle (J11, J15 regeneration 2), glycerol was supplied at a WHSV of 2.4 grams glycerol per gram catalyst per hour, and a GHSV of 8,994 per hour. The partial pressure of glycerol was 0.086, the partial pressure of water was 0.888, with a partial pressure of nitrogen being 0.026.

The regenerations represented above with reference to FIG. 6 are shown in tabular form in Table 5 below.

TABLE 5

| Catalyst | Cycle | TOS (min.) | GHSV (1/hr) | WHSV ($g_{gly}/g_{cat}$/hr) | glycerol | steam | nitrogen | wt % gly Feed | Acrolein Productivity ($g_{acrolein}/g_{cat}$/hr) | Conversion (%) | Acrolein Selectivity (%) |
|---|---|---|---|---|---|---|---|---|---|---|---|
| | | | | | \multicolumn{3}{c}{Partial Pressure (atm)} | | | | |
| Co(H$_2$PO$_4$)$_2$ | 1 | 0-10 | 8,150 | 2.44 | 0.084 | 0.891 | 0.026 | 32.47 | 1.312 | 100.0 | 88.3 |
| on HS-5 | | 10-20 | 8,150 | 2.44 | 0.084 | 0.891 | 0.026 | 32.47 | 1.282 | 100.0 | 86.3 |
| Fumed Silica | 2 | 0-10 | 8,150 | 2.44 | 0.084 | 0.891 | 0.026 | 32.47 | 1.319 | 99.7 | 89.1 |
| (26% PO4) | | 10-20 | 8,150 | 2.44 | 0.084 | 0.891 | 0.026 | 32.47 | 1.279 | 99.3 | 86.7 |
| | | 20-30 | 8,150 | 2.44 | 0.084 | 0.891 | 0.026 | 32.47 | 1.286 | 99.6 | 86.9 |
| | 3 | 0-10 | 8,150 | 2.44 | 0.084 | 0.891 | 0.026 | 32.47 | 1.316 | 99.9 | 88.7 |
| | | 10-20 | 8,150 | 2.44 | 0.084 | 0.891 | 0.026 | 32.47 | 1.294 | 99.8 | 87.3 |
| | | 20-30 | 8,150 | 2.44 | 0.084 | 0.891 | 0.026 | 32.47 | 1.290 | 99.7 | 87.1 |

Referring to FIGS. 8 and 9, multiple cycles including regeneration were performed using 32 minute cycle times and with regenerations using air at 550° C. Cycles 1-6 and 6-20 are shown, with the GHSV of cycles 1-6 being 34,192 per hour and the pressure of glycerol at 0.046 and the pressure of water at 0.848 and the pressure of nitrogen at 0.014, and the cycles being run at 280° C. Cycles 6-20 had a GHSV at 34,192 per hour, and the pressures of glycerol, water and nitrogen were the same as cycles 1-6.

The regenerations shown above with reference to FIGS. 8 and 9 above are shown in tabular form in Table 6 below.

TABLE 6

| Catalyst | Cycle | TOS (min.) | GHSV (1/hr) | WHSV ($g_{gly}/g_{cat}$/hr) | glycerol | steam | nitrogen | wt % gly Feed | Acrolein Productivity ($g_{acrolein}/g_{cat}$/hr) | Conversion (%) | Acrolein Selectivity (%) |
|---|---|---|---|---|---|---|---|---|---|---|---|
| | | | | | \multicolumn{3}{c}{Partial Pressure (atm)} | | | | |
| Co(H$_2$PO$_4$)$_2$ | 1 | 13 | 34,192 | 6.04 | 0.0467 | 0.952 | 0.0143 | 19.8 | 1.218 | 33.6 | 98.6 |
| on HS-5 | | 38 | 34,192 | 6.04 | 0.0467 | 0.952 | 0.0143 | 19.8 | 1.190 | 32.9 | 98.4 |
| Fumed Silica | | 97 | 34,192 | 6.04 | 0.0467 | 0.952 | 0.0143 | 19.8 | 0.885 | 25.7 | 93.7 |
| (26% PO4) | | 105 | 34,192 | 6.04 | 0.0467 | 0.952 | 0.0143 | 19.8 | 0.453 | 12.6 | 97.8 |
| | | 119 | 34,192 | 6.04 | 0.0467 | 0.952 | 0.0143 | 19.8 | 0.819 | 24.6 | 90.5 |
| | 2 | 2 | 34,192 | 6.04 | 0.0467 | 0.952 | 0.0143 | 19.8 | 2.291 | 69.4 | 89.8 |
| | | 17 | 34,192 | 6.04 | 0.0467 | 0.952 | 0.0143 | 19.8 | 2.028 | 61.9 | 89.1 |
| | | 32 | 34,192 | 6.04 | 0.0467 | 0.952 | 0.0143 | 19.8 | 1.999 | 61.1 | 89 |
| | 3 | 2 | 34,192 | 6.04 | 0.0467 | 0.952 | 0.0143 | 19.8 | 1.782 | 53.8 | 90.1 |
| | | 17 | 34,192 | 6.04 | 0.0467 | 0.952 | 0.0143 | 19.8 | 1.680 | 51.1 | 89.4 |
| | | 32 | 34,192 | 6.04 | 0.0467 | 0.952 | 0.0143 | 19.8 | 1.450 | 44.3 | 89.0 |
| | 4 | 2 | 34,192 | 6.04 | 0.0467 | 0.952 | 0.0143 | 19.8 | 1.960 | 58.4 | 91.3 |
| | | 17 | 34,192 | 6.04 | 0.0467 | 0.952 | 0.0143 | 19.8 | 1.419 | 42.7 | 90.4 |
| | | 32 | 34,192 | 6.04 | 0.0467 | 0.952 | 0.0143 | 19.8 | 1.386 | 41.8 | 90.2 |
| | 5 | 2 | 34,192 | 6.04 | 0.0467 | 0.952 | 0.0143 | 19.8 | 1.452 | 42.9 | 92.0 |
| | | 17 | 34,192 | 6.04 | 0.0467 | 0.952 | 0.0143 | 19.8 | 1.200 | 35.7 | 91.4 |
| | | 32 | 34,192 | 6.04 | 0.0467 | 0.952 | 0.0143 | 19.8 | 1.195 | 35.7 | 91.1 |
| | 6 | 2 | 34,192 | 6.04 | 0.0467 | 0.952 | 0.0143 | 19.8 | 1.500 | 44.1 | 92.5 |
| | | 17 | 34,192 | 6.04 | 0.0467 | 0.952 | 0.0143 | 19.8 | 1.155 | 34.2 | 91.9 |
| | | 32 | 34,192 | 6.04 | 0.0467 | 0.952 | 0.0143 | 19.8 | 1.057 | 31.6 | 91.0 |
| | 7 | 2 | 34,192 | 6.04 | 0.0467 | 0.952 | 0.0143 | 19.8 | 1.434 | 41.9 | 93.1 |
| | | 17 | 34,192 | 6.04 | 0.0467 | 0.952 | 0.0143 | 19.8 | 1.145 | 33.4 | 93.2 |
| | | 32 | 34,192 | 6.04 | 0.0467 | 0.952 | 0.0143 | 19.8 | 1.306 | 38.1 | 93.2 |
| | 8 | 2 | 34,192 | 6.04 | 0.0467 | 0.952 | 0.0143 | 19.8 | 1.348 | 39.4 | 93.0 |
| | | 17 | 34,192 | 6.04 | 0.0467 | 0.952 | 0.0143 | 19.8 | 0.997 | 29.1 | 93.2 |
| | | 32 | 34,192 | 6.04 | 0.0467 | 0.952 | 0.0143 | 19.8 | 1.039 | 30.4 | 92.9 |
| | 9 | 2 | 34,192 | 6.04 | 0.0467 | 0.952 | 0.0143 | 19.8 | 1.581 | 45.5 | 94.5 |
| | | 17 | 34,192 | 6.04 | 0.0467 | 0.952 | 0.0143 | 19.8 | 1.158 | 33.5 | 94.0 |
| | | 32 | 34,192 | 6.04 | 0.0467 | 0.952 | 0.0143 | 19.8 | 1.051 | 30.7 | 93.1 |
| | 10 | 2 | 34,192 | 6.04 | 0.0467 | 0.952 | 0.0143 | 19.8 | 1.209 | 34.9 | 94.2 |
| | | 17 | 34,192 | 6.04 | 0.0467 | 0.952 | 0.0143 | 19.8 | 1.220 | 35.4 | 93.7 |
| | | 32 | 34,192 | 6.04 | 0.0467 | 0.952 | 0.0143 | 19.8 | 1.136 | 33.0 | 93.8 |
| | 11 | 2 | 34,192 | 6.04 | 0.0467 | 0.952 | 0.0143 | 19.8 | 1.542 | 44.2 | 94.9 |
| | | 17 | 34,192 | 6.04 | 0.0467 | 0.952 | 0.0143 | 19.8 | 1.499 | 43.6 | 93.5 |
| | | 32 | 34,192 | 6.04 | 0.0467 | 0.952 | 0.0143 | 19.8 | 1.330 | 38.6 | 93.7 |
| | 12 | 2 | 34,192 | 6.04 | 0.0467 | 0.952 | 0.0143 | 19.8 | 1.297 | 37.5 | 94.1 |
| | | 17 | 34,192 | 6.04 | 0.0467 | 0.952 | 0.0143 | 19.8 | 1.256 | 36.1 | 94.6 |
| | | 32 | 34,192 | 6.04 | 0.0467 | 0.952 | 0.0143 | 19.8 | 1.185 | 34.2 | 94.2 |
| | 13 | 2 | 34,192 | 6.04 | 0.0467 | 0.952 | 0.0143 | 19.8 | 1.328 | 38.3 | 94.3 |
| | | 17 | 34,192 | 6.04 | 0.0467 | 0.952 | 0.0143 | 19.8 | 1.247 | 35.7 | 95.0 |
| | | 32 | 34,192 | 6.04 | 0.0467 | 0.952 | 0.0143 | 19.8 | 1.205 | 34.5 | 95.0 |
| | 14 | 2 | 34,192 | 6.04 | 0.0467 | 0.952 | 0.0143 | 19.8 | 1.221 | 34.9 | 95.2 |
| | | 17 | 34,192 | 6.04 | 0.0467 | 0.952 | 0.0143 | 19.8 | 1.413 | 40.7 | 94.4 |
| | | 32 | 34,192 | 6.04 | 0.0467 | 0.952 | 0.0143 | 19.8 | 1.256 | 36.1 | 94.6 |
| | 15 | 2 | 34,192 | 6.04 | 0.0467 | 0.952 | 0.0143 | 19.8 | 1.234 | 35.1 | 95.6 |
| | | 17 | 34,192 | 6.04 | 0.0467 | 0.952 | 0.0143 | 19.8 | 1.171 | 33.4 | 95.4 |
| | | 32 | 34,192 | 6.04 | 0.0467 | 0.952 | 0.0143 | 19.8 | 1.265 | 36.4 | 94.5 |

TABLE 6-continued

| Catalyst | Cycle | TOS (min.) | GHSV (1/hr) | WHSV ($g_{gly}/g_{cat}$/hr) | glycerol | steam | nitrogen | wt % gly Feed | Acrolein Productivity ($g_{acrolein}/g_{cat}$/hr) | Conversion (%) | Acrolein Selectivity (%) |
|---|---|---|---|---|---|---|---|---|---|---|---|
| | | | | | \multicolumn{3}{c}{Partial Pressure (atm)} | | | | |
| | 17 | 2 | 34,192 | 6.04 | 0.0467 | 0.952 | 0.0143 | 19.8 | 1.213 | 34.9 | 94.5 |
| | | 17 | 34,192 | 6.04 | 0.0467 | 0.952 | 0.0143 | 19.8 | 1.345 | 38.4 | 95.2 |
| | | 32 | 34,192 | 6.04 | 0.0467 | 0.952 | 0.0143 | 19.8 | 0.921 | 26.3 | 95.3 |
| | 18 | 2 | 34,192 | 6.04 | 0.0467 | 0.952 | 0.0143 | 19.8 | 1.254 | 35.9 | 95.0 |
| | | 17 | 34,192 | 6.04 | 0.0467 | 0.952 | 0.0143 | 19.8 | 1.242 | 35.6 | 94.9 |
| | | 32 | 34,192 | 6.04 | 0.0467 | 0.952 | 0.0143 | 19.8 | 1.360 | 39.0 | 94.8 |
| | 19 | 2 | 34,192 | 6.04 | 0.0467 | 0.952 | 0.0143 | 19.8 | 1.168 | 33.5 | 94.9 |
| | | 17 | 34,192 | 6.04 | 0.0467 | 0.952 | 0.0143 | 19.8 | 1.236 | 35.4 | 95.0 |
| | | 32 | 34,192 | 6.04 | 0.0467 | 0.952 | 0.0143 | 19.8 | 1.194 | 34.2 | 95.0 |
| | 20 | 2 | 34,192 | 6.04 | 0.0467 | 0.952 | 0.0143 | 19.8 | 1.270 | 36.1 | 95.7 |
| | | 17 | 34,192 | 6.04 | 0.0467 | 0.952 | 0.0143 | 19.8 | 1.246 | 35.9 | 94.4 |
| | | 32 | 34,192 | 6.04 | 0.0467 | 0.952 | 0.0143 | 19.8 | 1.189 | 34.0 | 95.2 |

In FIG. 10 multiple regenerations are shown. Cycle numbers 1-20 are shown run at a space velocity of 6.04 grams of glycerol per gram catalyst per hour, and a GHSV of 34,192 per hour. The pressure of glycerol is maintained at 0.046, the pressure of water 0.848, and the pressure of nitrogen 0.014. Regeneration was performed at 32 minute cycle times, with air at 550° C.

Referring to FIGS. 11 and 12, XRD analyses of catalyst are shown demonstrating phase stability. FIG. 11 demonstrates the phase stability of catalyst prepared according to the procedures described herein that include preparing a slurry. FIG. 12 demonstrates the phase stability of catalyst prepared according to the procedures described herein that include impregnating the support. With regard to the slurry prepared catalyst, the phase stability indicates that phase transformation to pyrophosphate and/or cyclic tetrametaphsophate took place. This phase transformation is consistent with catalyst poisoning resulting in catalyst that cannot be regenerating multiple times without rephosphating, for example. Alternatively, the phase transformation of FIG. 12 does not indicate phase transformation. As such the catalyst of the FIG. 12 may be regenerating multiple times.

Referring next to FIG. 13, dehydration using the impregnated catalyst is graphically depicted. More specifically a $Co(H_2PO_4)_2$/f-Silica (15 wt % $PO_4$) catalyst was prepared and exposed to glycerol under the following conditions: GHSV=9,387/hr, WHSV=1.266 ggly/gcat/hr, superficial velocity 0.476 m/s, gly feed 11.5 wt %, 2.25 mol % glycerol, 88.65 mol % $H_2O$, 9.11 mol % $N_2$, initial pressure drop of 3.5 psig.

Referring to FIG. 14, dehydration using a Co(III) catalyst of 22 wt % $PO_4$ as $Co(PO_4)_2$/HS-5 prepared as an impregnated catalyst is demonstrated in graphical form. To prepare the catalyst, $Co_3(PO_4)_2$ dissolved in 20% nitric acid IWI on HS-5, dried then calcined at 600° C. Dehydration was performed under the following conditions: GHSV=10,176/hr (1 atm), WHSV=0.893 ggly/gcat/hr, Superficial velocity=0.695 m/s, Pgly=0.029 atm, $PH_2O$=0.854 atm, $PN_2$=0.117 atm, Wt % gly=14.7%, DP=8.5 psi. The catalyst bed was configured as follows: 3.4 g catalyst (5.2 cm³ meas.), 30-60 mesh (Dp=0.595-0.25 mm), Length=27.1 cm, and ID=5.19 mm.

Referring to FIG. 15, dehydration of glycerol using a Co(III) catalyst of 23 wt % $PO_4$ Co(III)-Phosphate on HS-5 (slurry) can be performed and regenerated as indicated in the Fig. The catalyst can be prepared by adding Co(III) acetylacetonate added to $H_3PO_4$ (70 wt %) (P/Co=5) and this added to HS-5 support, with the resulting gel being dried and then calcined. The reactor bed can include 1.57 g catalyst, 30-60 mesh (Dp=0.595-0.25 mm), having a length of 27.1 cm and an ID=5.19 mm. Reactant can be provided to the reactor under the following conditions: GHSV=10,395/hr (1 atm), WHSV=1.93 ggly/gcat/hr, superficial velocity=0.682 m/s, Pgly=0.029 atm, $PH_2O$=0.854 atm, $PN_2$=0.117 atm, Wt % gly=14.7%, and DP=8.9 psi (initial). Analysis showed the initial material had a P/Co=4.45 and after use a P/Co=3.08.

Referring to FIG. 16 data obtained during the dehydration of glycerol with Fe-Phosphate Catalyst (25 wt % $PO_4$ as Fe-phosphate/HS-5 Silica (Slurry)) is shown. The reactor can be configured with 2.00 g catalyst, 30-60 mesh (Dp=0.595-0.25 mm), Length=27.2 cm, ID=5.19 mm. The first condition can be GHSV=10,395/hr (1 atm), WHSV=1.517 ggly/gcat/hr, superficial velocity=0.695 m/s, Pgly=0.029 atm, $PH_2O$=0.854 atm, $PN_2$=0.117 atm, Wt % gly=14.7%, and DP=9.4 psi (initial). The second condition noted can be GHSV=10,669/hr (1 atm), WHSV=1.517 ggly/gcat/hr, superficial velocity=0.712 m/s, Pgly=0.028 atm, $PH_2O$=0.826 atm, Pair=0.146 atm, Wt % gly=14.7%, and DP=14.0 psi (initial).

Referring to FIG. 17 data obtained during the dehydration of glycerol with Fe-Phosphate Catalyst and $CO_2$ as a diluent is shown (25 wt % $PO_4$ as Fe-phosphate/HS-5 Silica (Slurry)). The reactor can be configured with 2.00 g catalyst, 30-60 mesh (Dp=0.595-0.25 mm), having a length=27.2 cm and ID=5.19 mm. The initial reaction conditions can be GHSV=10,395/hr (1 atm), WHSV=1.517 ggly/gcat/hr, superficial velocity=0.682 m/s, Pgly=0.029 atm, $PH_2O$=0.854 atm, $PCO_2$=0.117 atm, Wt % gly=14.7%, and DP=9.4 psi. The noted second conditions can be GHSV=10,669/hr (1 atm), WHSV=1.517 ggly/gcat/hr, superficial velocity=0.712 m/s, Pgly=0.028 atm, $PH_2O$=0.826 atm, Pair=0.146 atm, and Wt % gly=14.7%. The noted third conditions can be GHSV=10,074/hr (1 atm), WHSV=1.517 ggly/gcat/hr, superficial velocity=0.677 m/s, Pgly=0.030 atm, $PH_2O$=0.897 atm, Pair=0.093 atm, and Wt % gly=14.7%.

Referring to FIG. 18 data obtained using excess $PO_4$ is shown. The catalyst can be equivalent to 26% $PO_4$ as 15 wt % $PO_4$ as $Co(H_2PO_4)_2$/f-Silica-Slurry with P/Co=~4. This catalyst can be used in a 26.1 cm long reactor having a ID=5.19 mm containing 2.25 g catalyst (5.5 cm³ meas.), 30-60 mesh (Dp=0.595-0.25 mm). The dehydration can take place under the following conditions: GHSV=4712/hr, WHSV=1.384 ggly/gcat/hr, superficial velocity=0.34 m/s, Pgly=0.0593 atm, $PH_2O$=0.7065 atm, $PN_2$=0.2342 atm, Wt % gly=30%, Initial DP (bed)=9.8 psi, and Initial DP (total)=13.4 psi. The data does demonstrate improved conversion and selectivity compared to other slurry prepared 15 wt % $PO_4$ on HS-5 fumed silica with stable performance for first 7 hours, and air regeneration at 600° C. recovering activity. Referring to FIG.

19 data is obtained demonstrating second air regeneration with a 15 wt % $PO_4$ as $Co(H_2PO_4)_2$/f-Silica (Slurry with P/Co=~4) as a continuation of the data shown in FIG. 18 above. During the $2^{nd}$ regeneration: glycerol flow can be stopped and held in steam flow for 20 minutes, air can be provided (at ~250 sccm), held for 5 minutes, the reaction zone can be ramped to 600° C. in 30 minutes, hold 2 hrs then cooled to 280° C. in 3 hrs (in air flow). Steam flow can be initiated for 20 minutes. before starting glycerol feed.

Referring to FIG. 20 provides data obtained while regenerating catalyst with rephosphating a 15 wt % $PO_4$ as $Co(H_2PO_4)_2$/f-Silica (Slurry with P/Co=~4). The reactor and catalyst loading is consistent with Co/P catalysts prepared herein as well as the reaction flows and conditions. For example Co/P-catalyst can be prepared according to the slurry method described above by making a solution of phosphoric acid ($H_3PO_4$) in water then slowly adding cobalt carbonate, $H_3PO_4$ to cobalt carbonate molar ratio between 3.5 and 4 as used a final loading on HS-5 fumed silica (Cabot) of ~15 wt % $PO_4$ in the form of $Co(H_2PO_4)_2$. In the reactor, 2.25 g of catalyst (0.25-0.6 mm diameter/30-60 mesh) can be loaded into a stainless steel reactor tube (5.2 mmID) for a total bed volume of ~5.5 mL and heated in nitrogen flow to 280° C. then steam introduced for 30 minutes. Reactant glycerol can be provided at GHSV=4,712/hr; WHSV=1.384 $g_{gly}/g_{cat}$/hr; partial pressures: glycerol=0.0593 atm; steam=0.7065 atm; nitrogen=0.2342 atm.

Catalyst can be regenerated between 16 and 24 hrs: glycerol feed stopped for 15 minutes (nitrogen and steam only); air introduced and nitrogen and steam turned off; ramped to 600° C. in 30 minutes and held for 2 hours; cooled in air to 280° C. (~3 hrs); air was turned off and nitrogen steam turned on for 15-30 minutes before feeding glycerol. Glycerol can again be provided at GHSV=4,712/hr; WHSV=1.384 $g_{gly}/g_{cat}$/hr; partial pressures: glycerol=0.0593 atm; steam=0.7065 atm; nitrogen=0.2342 atm.

Catalyst can be regenerated again, and glycerol provided at GHSV=4,712/hr; WHSV=1.384 $g_{gly}/g_{cat}$/hr; partial pressures: glycerol=0.0593 atm; steam=0.7065 atm; nitrogen=0.2342 atm rapid deactivation.

Upon loss of activity, glycerol flow can be stopped and the reactor containing the catalyst held in steam flow for 20 minutes, $N_2$ flow can be increased to 150 sccm for 10 minutes after water flow is turned off. Tributyl-phosphate can then be provided to the reactor at 1 mL/hr for 1 hr. The reactor can then be held in air flow (~250 sccm) overnight—~8 hrs, and steam flow provided for 20 minutes prior to starting glycerol feed. Catalyst activity can be recovered for ~1 hr prior to "normal deactivation pattern and may level out at ~20% conversion.

Referring to FIG. 21 provides data obtained while regenerating catalyst with rephosphating a 15 wt % $PO_4$ as $Co(H_2PO_4)_2$/f-Silica (Slurry with P/Co=~4). The reactor and catalyst loading is consistent with Co/P catalysts prepared herein as well as the reaction flows and conditions. Upon recognized loss of activity, the reactor and catalyst can be exposed to air at 600° C. for about 10 hrs, cooled to 280° C. in $N_2$ flow (150 sccm) and held for 1 hr. Tributyl-phosphate can then be exposed to the catalyst at 1 mL/hr for 1.75 hrs, then the catalyst can be held in air flow (~250 sccm) for 1 hr. Steam flow can be proved to the reactor and catalyst for 30 minutes prior to starting glycerol feed (or until tributyl-phosphate was no longer detected) exiting the reactor. Catalyst activity can be recovered with slightly improved selectivity (93% vs 91%).

Referring to FIG. 22 data obtained using a Rb-catalyst to perform dehydration is shown; 28% $RbH_2PO_4$ w/excess $H_3PO_4$/f-Silica (HS-5). The reactor is 26.0 cm in length and has an ID=5.19 mm, 2.81 g catalyst (5.5 cm3 meas.) can be added having a 30-60 mesh (Dp=0.595-0.25 mm). Under the first condition, reaction can be performed under the following conditions: GHSV=9,451/hr (1 atm), WHSV=1.079 ggly/gcat/hr, superficial velocity=0.683 m/s, Pgly=0.029 atm, $PH_2O$=0.855 atm, $PN_2$=0.117 atm, Wt % gly=14.7%, and DP=8.0 psi. As noted a second condition can be provided and that condition can include the following: reactor at 290° C., GHSV=2766/hr (1 atm), WHSV=1.079 ggly/gcat/hr, superficial velocity=0.2 m/s, Pgly=0.098 atm, $PH_2O$=0.503 atm, $PN_2$=0.399 atm, Wt % gly=50%, and DP=6.5 psi (initial). Under the third condition noted, the reactor is maintained at 290° C., GHSV=6409/hr(1 atm), WHSV=1.079 ggly/gcat/hr, superficial velocity=0.463 m/s, Pgly=0.042 atm, $PH_2O$=0.217 atm, $PN_2$=0.741 atm, Wt % gly=50%, and DP=6.5 psi. The Rb-catalyst demonstrated substantial robustness.

Referring to FIG. 23, XRD data of unused Rb-catalyst is shown and in FIG. 24 XRD data of used Rb-catalyst is shown. This XRD demonstrate the lack of phosphate leaching occurring during dehydration and subsequent regeneration.

Referring to FIG. 25 data obtained using a Rb-catalyst to perform dehydration is shown; 28% $RbH_2PO_4$ w/excess $H_3PO_4$/f-Silica (HS-5) and additional data obtained as the process continued is shown in FIG. 26. About 2.76 g catalyst (5.7 $cm^3$ meas.) with 30-60 mesh (Dp=0.595-0.25 mm) can be loaded into a 27 cm long reactor have an ID=5.19 mm. The first condition noted can be performed with a reactor at 290° C. and: GHSV=4756/hr (1 atm), WHSV=1.80 ggly/gcat/hr, Pgly=0.09 atm, $PH_2O$=0.462 atm, $PN_2$=0.448 atm, Wt % gly=30 wt %, and DP=6.2 psi.

The second condition noted can be performed with a reactor at 300° C. and: GHSV=3734/hr (1 atm), WHSV=1.10 ggly/gcat/hr, Pgly=0.07 atm, $PH_2O$=0.36 atm, $PN_2$=0.57 atm, Wt % gly=50 wt %, and DP=4.5 psi. Under condition 2a, the reactor can be 300° C. and GHSV=5886/hr (1 atm), WHSV=1.1 ggly/gcat/hr, Pgly=0.045 atm, $PH_2O$=0.228 atm, $PN_2$=0.728 atm, and Wt % gly=50%.

The third condition noted can be performed with a reactor at 300° C. and: GHSV=5822/hr (1 atm), WHSV=1.1 ggly/gcat/hr, Pgly=0.045 atm, $PH_2O$=0.231 atm, $PN_2$=0.365 atm, PAir=0.359 atm, and Wt % gly=50%.

The fourth condition noted can be performed with a reactor at 300° C. and: GHSV=5822/hr (1 atm), WHSV=1.1 ggly/gcat/hr, Pgly=0.045 atm, $PH_2O$=0.229 atm, $PN_2$=0.637 atm, PAir=0.089 atm, and Wt % gly=50%.

The fifth condition noted can be performed with a reactor at 300° C. and: GHSV=9099/hr (1 atm), WHSV=1.1 ggly/gcat/hr, Pgly=0.029 atm, $PH_2O$=0.856 atm, Pair=0.115 atm, and Wt % gly=50%.

Referring to FIGS. 25 and 26, the dehydration process continued >60 hrs on stream before deactivation with 78% acrolein selectivity, 15% acetol selectivity. Addition of air improved conversion (100%) and selectivity (to 70%), and reduced acetol formation and dimer formation. Catalyst was regenerated.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

What is claimed is:

1. A glycerol dehydration method comprising exposing glycerol to a catalyst, the catalyst comprising a fumed support material, phosphate, and at least one or more metals from groups 2-12 of the periodic table or K, Cs, or Rb, the exposing forming one or both of acrolein and acetol.

2. The method of claim 1 wherein the glycerol is a co-product of biofuel production.

3. The method of claim 1 wherein the glycerol is comprised by a reactant mixture, the mixture comprising 3-70% (wt./wt.) glycerol.

4. The method of claim 3 wherein the mixture comprises at least about 30% (wt./wt.) glycerol.

5. The method of claim 3 wherein the reactant mixture further comprises one or more of N2, CO2 and H2O.

6. The method of claim 5 wherein either or both of the N2 and CO2 is less than 1% (wt./wt.) of the reactant mixture.

7. The method of claim 3 wherein the reactant mixture has a temperature of at least about 100° C. prior to being exposed to the catalyst.

8. The method of claim 1 wherein the catalyst is maintained at a temperature of between 250° C. and 350° C. during the exposing.

9. The method of claim 1 wherein the fumed support material comprises Si.

10. The method of claim 1 wherein the one or more metals includes Co and the phosphate is in the form of dihydrogen phosphate.

11. A glycerol dehydration catalyst regeneration method comprising:
providing a used glycerol dehydration catalyst, the catalyst comprising a fumed support material, phosphate, and at least one or more metals from groups 2 12 of the periodic table and/or Rb, K, and Cs; and
exposing the used catalyst to either N2 alone and/or air while maintaining a temperature of the catalyst above 200° C. to regenerate the catalyst.

12. The method claim 11 wherein the exposing comprises passing either N2 alone and/or air over the catalyst while maintaining a temperature of the catalyst above 550° C.

13. The method claim 11 wherein the exposing comprises:
passing N2 alone over the used catalyst while maintaining a temperature of the catalyst above 200° C.; and
passing air over the used catalyst while maintaining a temperature of the catalyst above 550° C.

14. The method of claim 13 wherein the passing the N2 alone over the used catalyst is performed prior to passing the air over the used catalyst.

15. The method of claim 11 further comprising monitoring CO2 evolution from the catalyst.

16. A glycerol dehydration system comprising:
a reactor coupled to at least two conduits, one of the two conduits configured to convey reactants to the reactor, and the other of the two conduits configured to convey products from the reactor; and
a catalyst within the reactor, the catalyst comprising a fumed support material, phosphate, and at least one or more metals from groups 2-12 of the periodic table and/or Rb, K, and Cs.

17. The glycerol dehydration system of claim 16 wherein the catalyst comprises fumed Si, dihydrogen phosphate, and Co.

18. The glycerol dehydration system of claim 16 wherein the one conduit is configured to vaporize its contents prior to conveying same to the reactor.

19. The glycerol dehydration system of claim 16 wherein the reactor is configured to be programmably heated between the temperatures of 100° C. and 600° C.

20. A chemically synthetic dehydration process comprising:
exposing a multihydric reactant to a phosphorous comprising catalyst within a reactor to form a dehydration product, wherein the phosphorous comprising catalyst comprises a fumed support material, phosphate, and at least one pr more metals from groups 2-12 of the periodic table and/or Rb, K, and Cs;
ceasing the providing of the reactant to the reactor; and
after ceasing the providing of the reactant, providing a phosphorous comprising material to the reactor, the phosphorous comprising material increasing the amount of phosphorous in the dehydration catalyst; and
after providing the phosphorous comprising material, again providing reactant to the reactor.

21. The process of claim 20 wherein the multihydric reactant comprises glycerol.

22. The process of claim 20 wherein the dehydration product comprises one or both of acrolein and acetol.

23. The process of claim 20 wherein the phosphorous comprising material comprises an organophosphate.

24. The process of claim 23 wherein the organophosphate comprises trimethylphosphate.

* * * * *

UNITED STATES PATENT AND TRADEMARK OFFICE
CERTIFICATE OF CORRECTION

PATENT NO. : 8,907,135 B2  
APPLICATION NO. : 13/892143  
DATED : December 9, 2014  
INVENTOR(S) : James J. Strohm et al.

It is certified that error appears in the above-identified patent and that said Letters Patent is hereby corrected as shown below:

Title Page

Page 2, Column 1 (56) References Cited – Replace "PCT/US2010/061373WrittenOpinio, Oct. 7, 2011, Battelle Memorial Institute." with --PCT/US2010/061373 Written Opinion, Oct. 7, 2011, Battelle Memorial Institute.--

Page 2, Column 2 (56) References Cited – Replace "Faro, Arnaldo C., et al, "Cumene hydrocracking and tiophene HDS on niobia-supported Ni, Mo and Ni-Mo catalaysts" Catalysis Today, vol. 118, 2006, pp. 402-409, XPOO2511927 Abstract." with --Faro, Arnaldo C., et al, "Cumene hydrocracking and tiophene HDS on niobia-supported Ni, Mo and Ni-Mo catalysts" Catalysis Today, vol. 118, 2006, pp. 402-409, XPOO2511927 Abstract.--

Page 2, Column 2 (56) References Cited – Replace "CN 2010800573893 Search Report, Nov. 7, 2013, Battalle Memorial Institute." with --CN 2010800573893 Search Report, Nov. 7, 2013, Battelle Memorial Institute.--

Specification

Column 8, line 33 – Replace "be couple to" with --be coupled to--

Column 9, line 53 – Replace "system deceases" with --system decreases--

Column 11, line 45 – Replace "can increasing" with --can increase--

Column 15, line 47 – Replace "carbon by product" with --carbon byproduct--

Column 19, line 43 – Replace "(15 wt % PO$_4$)" with --(15wt% PO$_4$)--

Signed and Sealed this  
Twenty-third Day of February, 2016

Michelle K. Lee  
*Director of the United States Patent and Trademark Office*

CERTIFICATE OF CORRECTION (continued)
U.S. Pat. No. 8,907,135 B2

Specification

Column 21, line 49 – Replace ""normal deactivation pattern and" with
--"normal deactivation pattern" and--

Claims

Column 23, line 34, claim 11 – Replace "groups 2 12" with --groups 2-12--

Column 23, line 39, claim 12 – Replace "method claim" with --method of claim--

Column 23, line 42, claim 13 – Replace "method claim" with --method of claim--

Column 24, line 29, claim 20 – Replace "one pr more" with --one or more--